United States Patent [19]
Seaton et al.

[11] Patent Number: 5,853,666
[45] Date of Patent: Dec. 29, 1998

[54] OPTICAL READER AND SAMPLE CARD TRANSPORT STATIONS FOR BIOLOGICAL SAMPLE TESTING MACHINE

[75] Inventors: William Ernest Seaton, Chesterfield; Mark Joseph Fanning, Florissant; David B. Shine, University City; Craig Drager, Ballwin, all of Mo.

[73] Assignee: bioMérieux Vitek, Inc., Hazelwood, Mo.

[21] Appl. No.: 798,093

[22] Filed: Feb. 12, 1997

Related U.S. Application Data

[62] Division of Ser. No. 604,472, Feb. 21, 1997, Pat. No. 5,670,375.

[51] Int. Cl.⁶ .................................................. G01N 35/02
[52] U.S. Cl. .......................... 422/65; 422/63; 422/82.05; 422/82.09; 435/34; 435/288.4; 435/288.7; 435/808; 436/43; 436/47; 436/48; 436/165; 356/246; 356/341
[58] Field of Search ................................. 422/63, 64, 65, 422/82.05, 104, 82.09; 436/43, 47, 48, 164, 165; 435/34, 288.4, 288.7, 808; 356/246, 341

[56] References Cited

U.S. PATENT DOCUMENTS

| | | | |
|---|---|---|---|
| 4,118,280 | 10/1978 | Charles et al. | 195/127 |
| 4,141,444 | 2/1979 | Kulberg et al. | |
| 4,236,825 | 12/1980 | Gilford et al. | 356/414 |
| 4,372,783 | 2/1983 | Lackie . | |
| 4,448,534 | 5/1984 | Wertz et al. | |
| 4,477,190 | 10/1984 | Liston et al. | |
| 4,501,970 | 2/1985 | Nelson . | |
| 4,580,895 | 4/1986 | Patel . | |
| 4,626,684 | 12/1986 | Landa . | |
| 4,632,808 | 12/1986 | Yamamoto et al. | |
| 4,661,711 | 4/1987 | Harjunmaa . | |
| 4,673,657 | 6/1987 | Christian . | |
| 4,678,752 | 7/1987 | Thorne et al. | 435/291 |
| 4,685,801 | 8/1987 | Minekane . | |

(List continued on next page.)

FOREIGN PATENT DOCUMENTS

| | | |
|---|---|---|
| 156398 | 2/1981 | Germany . |
| 215398 | 4/1983 | Germany . |
| 242869 | 12/1985 | Germany . |
| 248879 | 5/1986 | Germany . |
| 1574014 | 10/1987 | U.S.S.R. . |
| 8400609 | 2/1984 | WIPO . |

OTHER PUBLICATIONS bioMérieux Vitek, Inc., Brochure—Vitek© System (1995).
Manual—Vitek© Reader Procedures Manual, pp. 9–1 to 9–5 (1991).

*Primary Examiner*—Long V. Le
*Attorney, Agent, or Firm*—McDonnell Boehnen Hulbert & Berghoff

[57] ABSTRACT

A sample card transport station moves a test sample card from an incubation station for the card to a transmittance and fluorescence optical station in a sample testing machine. The sample card transport station has a drive belt and an associated stepper motor. The belt supports the card from one side of the card. A ledge having a card slot is disposed above the belt. The card is snugly received within the card slot, and supported from below by the drive belt and rollers for the belt. When the motor turns the belt, the belt grips the card and slides the card along the slot to the optical stations, without any slippage between the belt and the card. This construction provides for precise control over the movement of the card.

The fluorescence station has a linear flash lamp that illuminates a column of the wells of the cards simultaneously. A reference detector and dichromatic beam splitter design is used to insure that the fluorescence measurements are independent of lamp output changes over time. A solid reference is mounted to an optical shuttle and moved into the optical path to calibrate the fluorescence photodiode detectors.

9 Claims, 22 Drawing Sheets

U.S. PATENT DOCUMENTS

| | | |
|---|---|---|
| 4,710,352 | 12/1987 | Slater et al. . |
| 4,755,054 | 7/1988 | Ferree . |
| 4,826,660 | 5/1989 | Smith et al. . |
| 4,861,554 | 8/1989 | Sakuma . |
| 4,877,965 | 10/1989 | Dandliker et al. . |
| 4,945,250 | 7/1990 | Bowen et al. . |
| 5,008,082 | 4/1991 | Shaw . |
| 5,061,076 | 10/1991 | Hurley . |
| 5,073,029 | 12/1991 | Eberly et al. . |
| 5,094,531 | 3/1992 | Garner et al. . |
| 5,232,665 | 8/1993 | Burkovich et al. .................. 422/65 |
| 5,306,618 | 4/1994 | Prober et al. . |
| 5,337,139 | 8/1994 | Shirasawa . |
| 5,340,747 | 8/1994 | Eden ................................. 436/172 |
| 5,358,691 | 10/1994 | Clark et al. . |
| 5,366,903 | 11/1994 | Lundsgaard et al. . |
| 5,374,395 | 12/1994 | Robinson et al. .................. 422/64 |
| 5,399,315 | 3/1995 | Paz-Pujalt et al. . |
| 5,401,465 | 3/1995 | Smethers et al. . |
| 5,417,922 | 5/1995 | Markin et al. . |

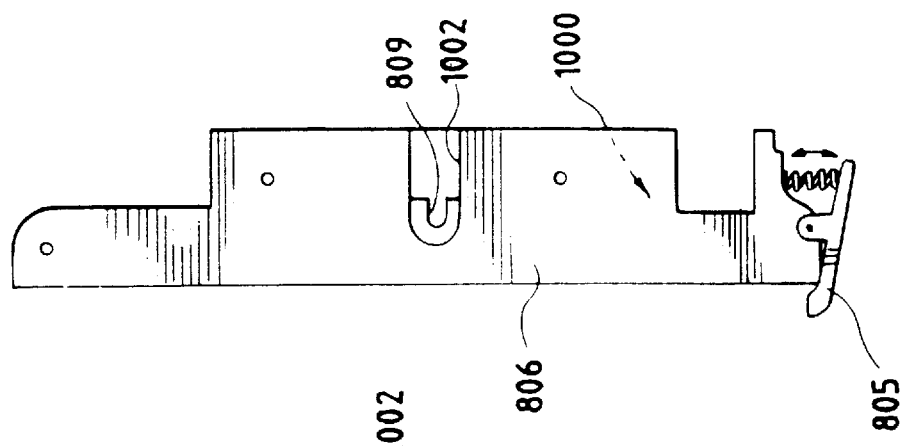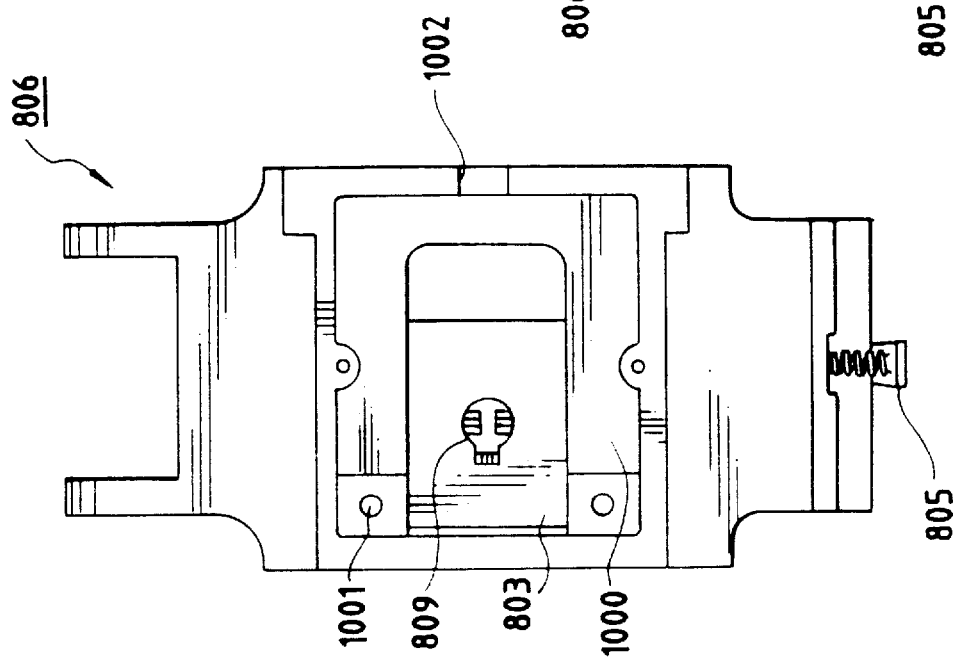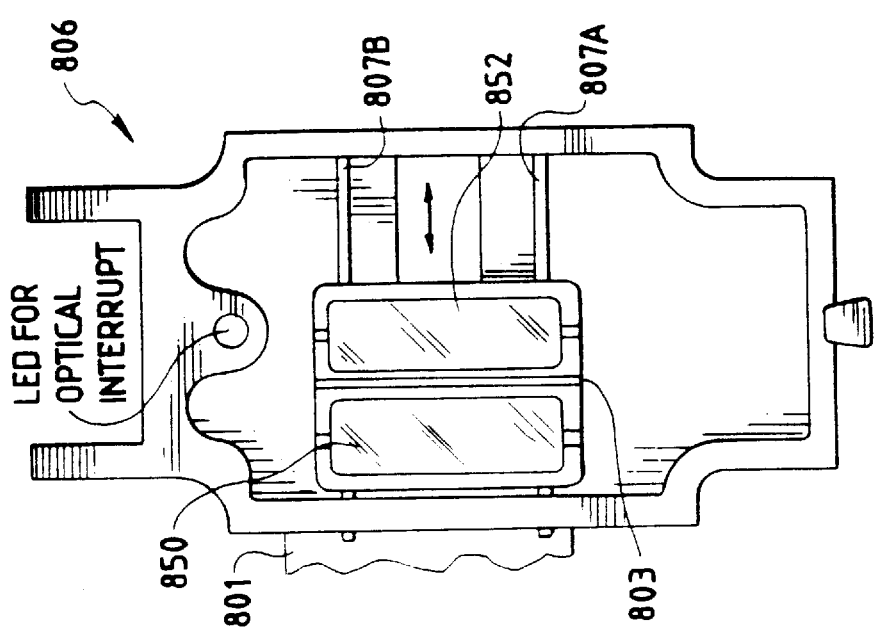

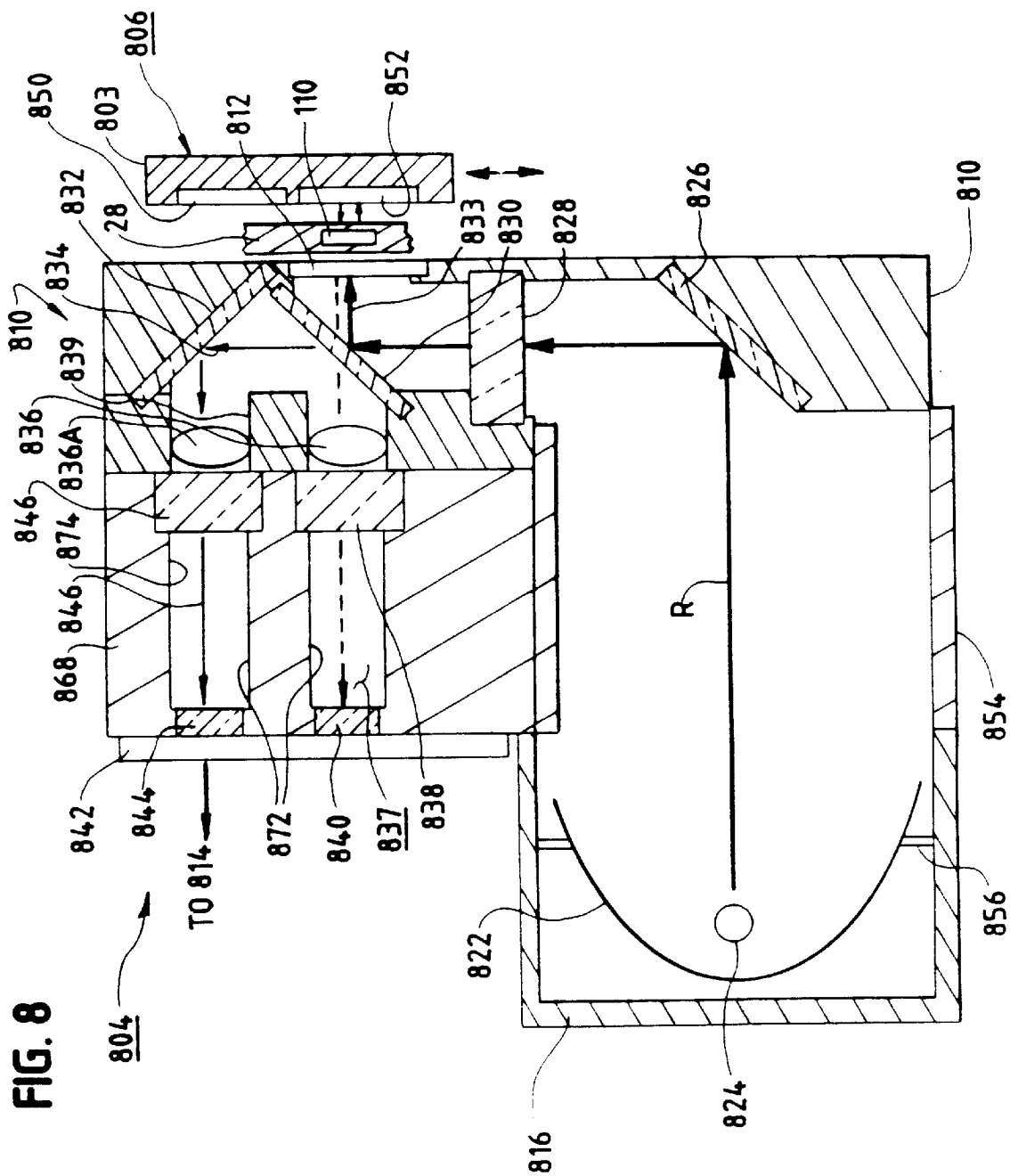

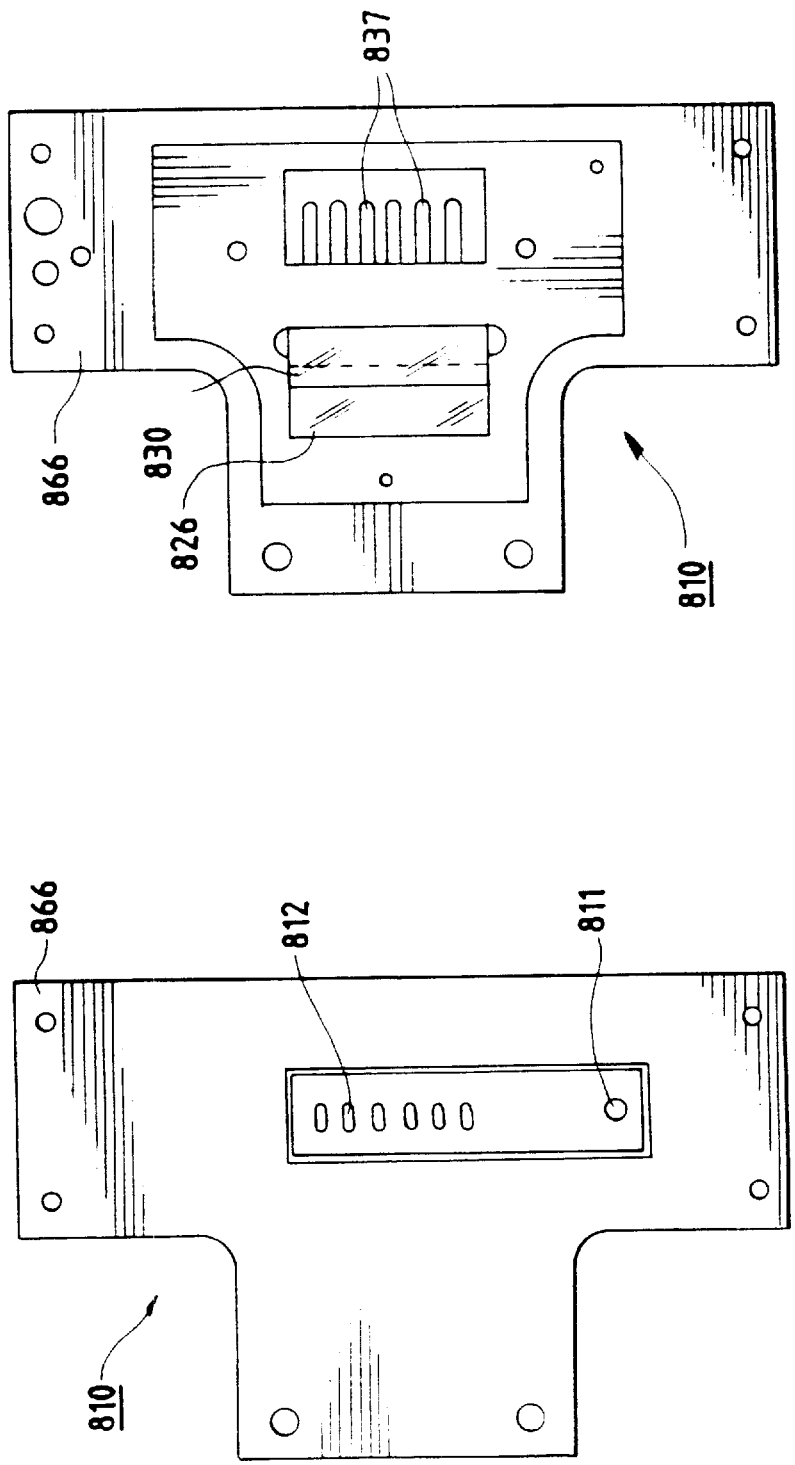

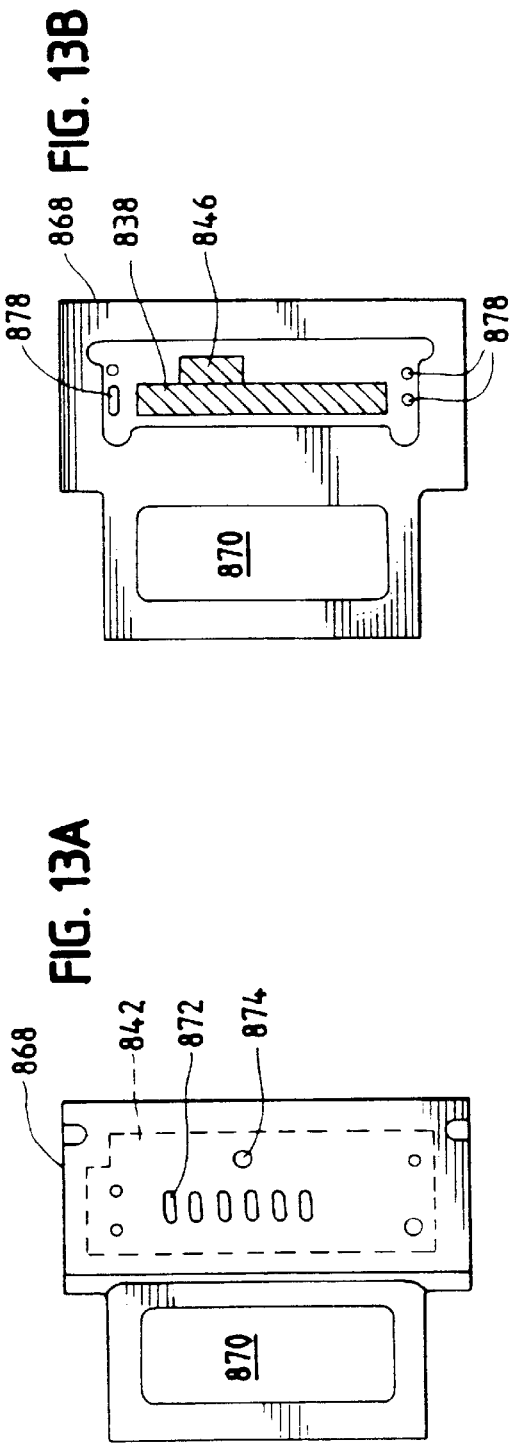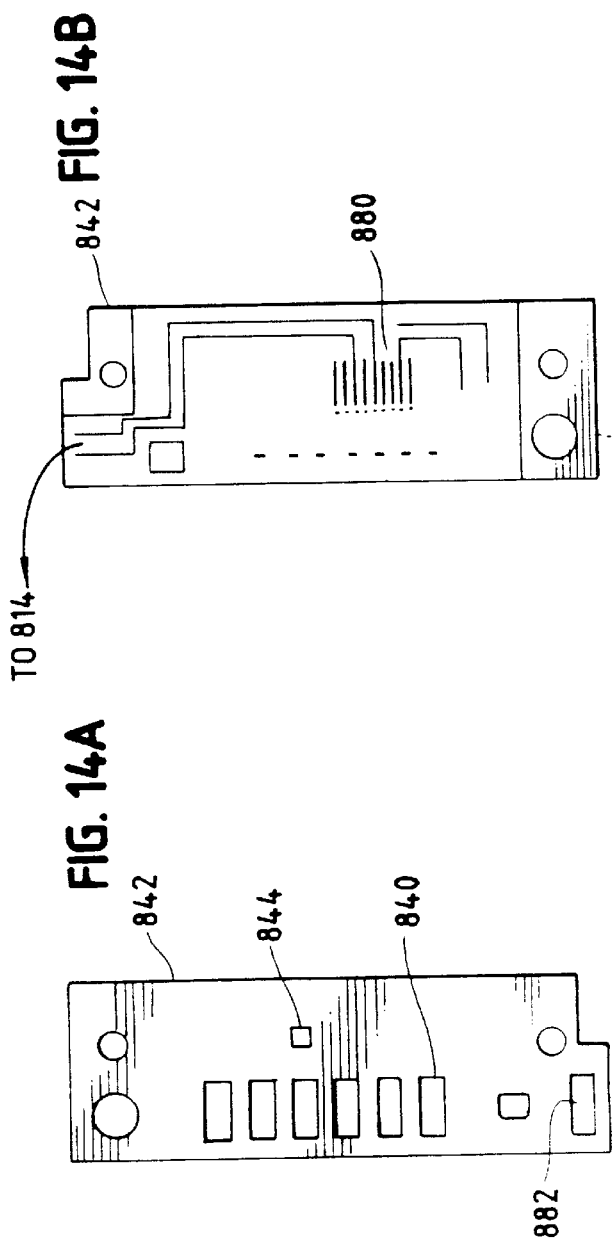

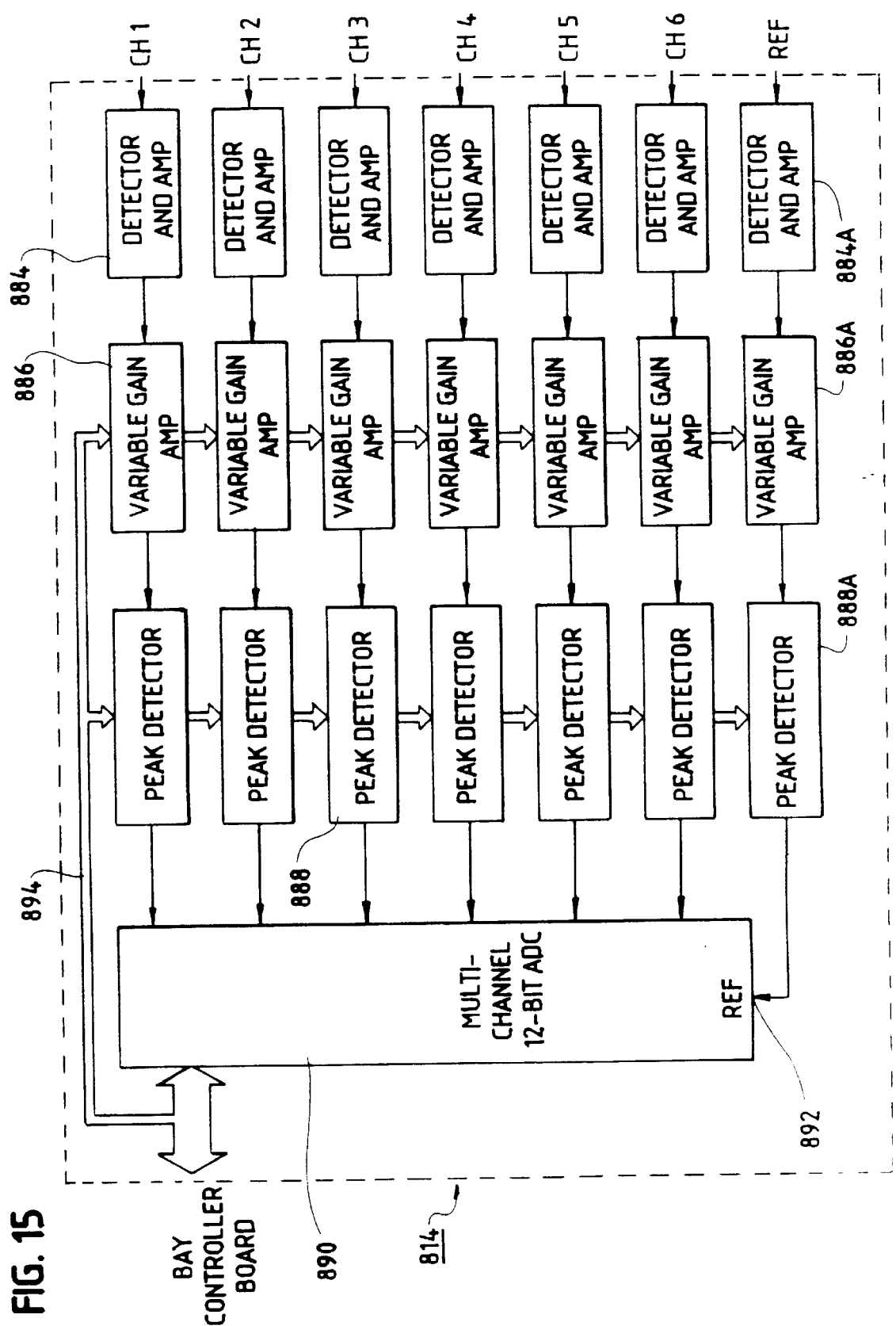

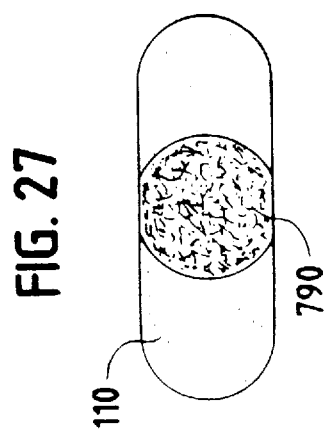
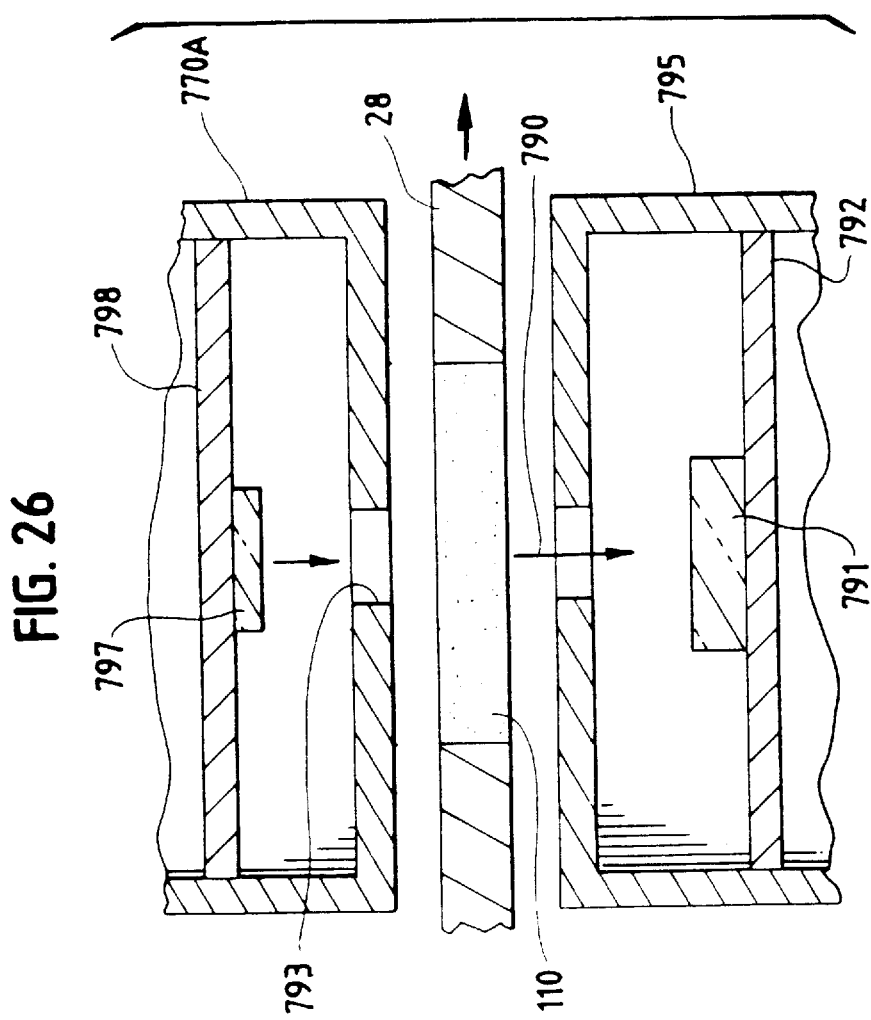

OPTICAL READER AND SAMPLE CARD TRANSPORT STATIONS FOR BIOLOGICAL SAMPLE TESTING MACHINE

This is a divisional of application Ser. No. 08/604,472, filed Feb. 21, 1997, U.S. Pat. No. 5,670,375.

BACKGROUND OF THE INVENTION

A. Field of the Invention

This invention relates to the field of optical systems that conduct analysis of biological test samples, and the mechanical systems that place the test samples into position for reading by the optical system. These systems are typically found in automated microbiology, immunoassay and biological sample testing machines, and related diagnostic or analytical machines such as found in infectious disease, immuno-chemistry and nucleic acid probe systems.

B. Description of Related Art

It is known in the art that biological samples can be subject to optical analysis using various techniques, two of which are transmittance and fluorescence optical analysis. The purpose of the analysis may be to identify an unknown biological agent in the sample, test the sample to determine the concentration of a substance in the sample, or determine whether the biological agent is susceptible to various antibiotics. The analysis may further identify the concentration of antibiotic that would be effective in treating an infection containing the agent.

A technique has been developed for conducting optical analysis of biological samples that involves the use of a sealed test sample card containing a plurality of small sample wells or reaction sites. During manufacture of the cards, e.g., for microbiological analysis of test samples, the sample wells are loaded with growth media for different biological agents, or else various concentrations of different antibiotics. Fluid containing the biological sample enters the card via an L-shaped transfer tube extending outwardly from a transfer tube port in the card. An internal fluid passageway structure allows the fluid to migrate from the transfer tube port to the wells of the card.

To load the card with fluid, the transfer tube is placed in a test tube containing a biological sample, and the card/transfer tube/test tube assembly is placed in a vacuum filling and sealing machine, such as the Vitek® Filler Sealer (from bioMérieux Vitek, Inc.). The filling and sealing machine generates a vacuum, the release of which causes the fluid in the test tube to be drawn into the wells of the sample card.

After the wells of the card are loaded with the sample, the transfer tube is cut off and melted, sealing the interior of the card, and the card is placed into a reading and incubation machine. The reading and incubating machine incubates the cards at a desired temperature. An optical reader is provided for conducting transmittance testing of the wells of the card. Basically, the cards are stacked in columns in the reading machine, and an optical system moves up and down the column of cards, pulling the cards into the transmittance optics one at a time, reading the cards, and placing the cards back in the column of cards. The Vitek® reading machine is described generally in the Charles et al. patent, U.S. No. 4,188,280.

The ability of the optical reading system to take accurate reads of the sample wells is a function of several variables, such as the presence of air bubbles in the sample wells, the accurate placement of the growth or antibiotic medium in the sample wells, the number of reads obtained during the incubation of the cards, and the sophistication of the optics of the reading machine. Obviously, to improve the analytical capabilities of the machine, the performance of the optical reading system is critical.

In addition to the Charles et al. patent mentioned above, prior art patents relating to the general subject of optical systems for analysis of biological samples include U.S. Pat. No. 4,626,684 to Landa, and U.S. Pat. No. 5,340,747 to Eden. Other background references include U.S. Pat. No. 4,477,190; WIPO published patent application WO 84/00609 (Heller); and U.S. Pat. 5,372,783 to Lackie. The patent to Robinson et al., U.S. Pat. No. 5,374,395, discloses a diagnostic instrument in which a carousel holds test packs during incubation periods and rotates the test packs past an optical reader that senses the presence of an analyte in the sample. Prior art systems for transporting specimen carriers in diagnostic machines include the above-referenced Charles et al. patent, U.S. Pat. No. 5,417,922 to Markin et al; U.S. Pat. No. 4,236,825 to Gilford et al., and the above-referenced Robinson et al. patent.

An object of the invention is to provide an optical reading system for reading test sample cards that enables a rapid and precise identification and analysis of the specimens. The invention incorporates a unique fluorescence-based detection substation and an advanced multiwavelength transmittance testing substation, enabling both types of analysis to be performed automatically for the cards.

The fluorescence substation achieves a significant throughput by simultaneously analyzing multiple sample wells using a single fluorescence light source and multiple detector elements in a single assembly. Reliability, compactness, and repeatability in the fluorescence measurements are much improved over prior art systems.

Furthermore, prior art multiple channel fluorometers typically use a single light source that is split into multiple channels using optical fibers, which direct the light through sample wells onto a single multiplexed detector or separate individual detectors. These systems tend to be large and complex assemblies requiring precise positioning of optical fibers. In addition, energy and signal losses in the optical fibers reduce the efficiency of the system. The present system performs true simultaneous readings of multiple sample wells using a single excitation source and multiple emission detection devices without the need for separate optical fibers or excitation and emission pathways. The fluorescence substation further includes a lamp reference detector, enabling precise readings of the wells of the card independent of any changes in the output of the excitation light source.

The inventive fluorescence substation also includes an optical shuttle assembly and solid reference source that allows for automatic calibration of the photodiode detectors when the cards are not being read. To calibrate the system, the shuttle moves the solid reference into the optical path. The solid reference is illuminated by the lamp, and emits radiation at the wavelength of the fluorophores. The radiation is received by the photodetectors, and the outputs can be calibrated by adjusting moveable gain amplifiers, insuring accurate measurements of fluorescence from the wells of the card.

The present invention also provides for a sample card transport system for precisely moving the test sample card relative to the optical system so as to permit numerous data sets in each reading cycle. The sample card transport system moves the cards from an incubation chamber to the transmittance and/or fluorescence optics substations, where readings are taken of the card. At the transmittance substation, multiple reads of the wells are taken at several positions across the well, generating a large number of data sets. Once the test is complete, the sample card transport system moves the card to a card output tray. If more testing is needed, the card is moved back to the carousel. The precise movement features of the present test sample card transport system are believed to be unique.

These and other objects, advantages and features of the invention will become more apparent from the following detailed description of presently preferred embodiments of the invention.

SUMMARY OF THE INVENTION

In one aspect of the invention, a transport system is provided for moving a test sample card having a plurality of sample wells and first and second edges relative to an optical system for reading the sample wells. The transport system has a support bulkhead for supporting the optical system and a ledge mounted to the bulkhead for maintaining alignment of the card relative to the optical system. The ledge defines a card slot for receiving the first edge of the card, the slot defining a card travel direction. A drive subassembly is mounted to the support bulkhead, and includes:

a) a drive belt supported by at least one roller and movable relative to the ledge in a direction parallel to the card travel direction, the drive belt engaging the second edge of the card to move the card relative to the optical system;

b) means for driving the belt; and c) spring means for biasing the drive subassembly towards the ledge so as to maintain pressure between the card, the ledge means and the belt.

The drive belt slides the card relative to the ledge in the card travel direction without significant slippage between the drive belt and the second edge of the card, thereby permitting the motor to move the card relative to the optical system with substantial precision.

The substantial precision in moving the card relative to the optical system is particularly taken advantage of in transmission optical analysis of the wells of the card. The presence of air bubbles in the sample well can prevent accurate reading of the sample wells, since the air bubble creates a zone in the well that is nearly opaque, allowing little of the transmittance illumination in that zone to impinge on the detector. This problem is overcome by causing the motor and drive belt to move the card in a plurality of discrete steps in the forward or the reverse direction across the width of the well, so as to enable a plurality of transmittance measurements at different locations of the wells in the card. For example, the card may be moved into fourteen different positions relative to the source and detector, and the transmittance source flashed rapidly at 10 flashes per position, resulting in 140 data points for each well. Simple statistical analysis of the data can detect the presence of an air pocket in the well, but enough data is obtained from the other portions of the well outside of the air pocket to permit adequate transmittance measurement.

The optical reading system further includes a fluorescence optical station. The wells of the card are loaded with a fluorophore during manufacture that is released or inhibited by biological or chemical processes once the wells are loaded with biological samples. The fluorophores are excitable upon the receipt of radiation at a light excitation wavelength and emit radiation at a light emission wavelength. A preferred fluorescence station comprises:

(a) an excitation lamp for simultaneously illuminating the column of wells with an excitation light at the excitation wavelength;

(b) a dichromatic beam splitter reflecting a portion of the excitation light from the excitation lamp simultaneously to the column of wells, the beam splitter at least partially transparent to radiation at the emission wavelength;

(c) a reference detector receiving excitation light passing from the excitation lamp through the beam splitter;

(d) a reflector assembly disposed opposite the wells from the excitation lamp and beam splitter for reflecting excitation light passing through the wells back into the wells;

(e) a plurality of detectors, one for each of the sample wells, the detectors receiving radiation at the emission energy level transmitted from the sample wells through the beam splitter; and (f) a peak detector circuit for comparing the output of the reference detector and the plurality of detectors. The inclusion of the reference detector and a beam splitter at least partially transmissive to excitation radiation enables a ratio of detector output to reference output to be calculated in the station electronics. This ratio of signals provides for consistent measurements of fluorescence from the wells, independent of a change in output of the excitation lamp over time.

In a preferred form of the invention, the excitation light passes from the beam splitter to the well and reflection assembly along the same optical path. The reflection assembly further comprises an optical shuttle having a solid reference source that emits radiation at the emission energy level of the fluorophore. The optical shuttle moves the reference source into the optical path. When the solid reference source is positioned in the optical path and operated to emit radiation, a simple calibration of the detectors may be made such that they all produce the same signal for a given output from the reference source as they did at an initial calibration with a control reference. A preferred solid reference source is a phosphorescent material (such as Europium) that emits radiation at the same wavelength as the fluorophores in the well when it is illuminated by the excitation lamp.

These and many other features and advantages of the invention will be more apparent from the following detailed description of preferred embodiments of the invention.

BRIEF DESCRIPTION OF THE DRAWINGS

Presently preferred embodiments of the invention are depicted in the drawings, wherein like reference numerals refer to like elements in the various views, and wherein:

FIG. 7A is a plan view of the front of the reflector assembly of FIG. 7;

FIG. 7B is a plan view of the rear of the reflector assembly of FIG. 7;

FIG. 7C is a side view of the reflector assembly of FIG. 7;

FIG. 8 is a sectional view of the fluorescence optical substation of FIG. 7;

FIG. 10 is a front view of the optical head of FIG. 7, showing the optical interrupt channel and the six channels for reading six wells of the card;

FIG. 11 is a rear view of the optical head of FIG. 7;

FIG. 13A is a rear view of the optical interface block of FIG. 7, showing the detector board mounted to the optical interface block;

FIG. 13B is a front view of the optical interface block of FIG. 13A, showing the placement of the bandpass filters in front of the optical channels;

FIG. 14A is a front view of the detector board of FIG. 8, showing the photodiode detectors that are placed behind the six channels of the optical interface block of FIG. 13;

FIG. 14B is a rear view of the detector board of FIG. 14A;

FIG. 15 is a block diagram of a preferred peak detector board for the fluorescence substation of FIG. 15;

FIG. 26 is a sectional view of the transmittance substation of FIG. 24, showing the relationship between the LED transmittance light source, sample well, and photodiode detector;

FIG. 27 is an elevational view of the sample well and LED output for the transmittance substation of FIG. 24.

DETAILED DESCRIPTION OF THE PREFERRED EMBODIMENT

Overview of Preferred Sample Testing Machine

Figure 1:
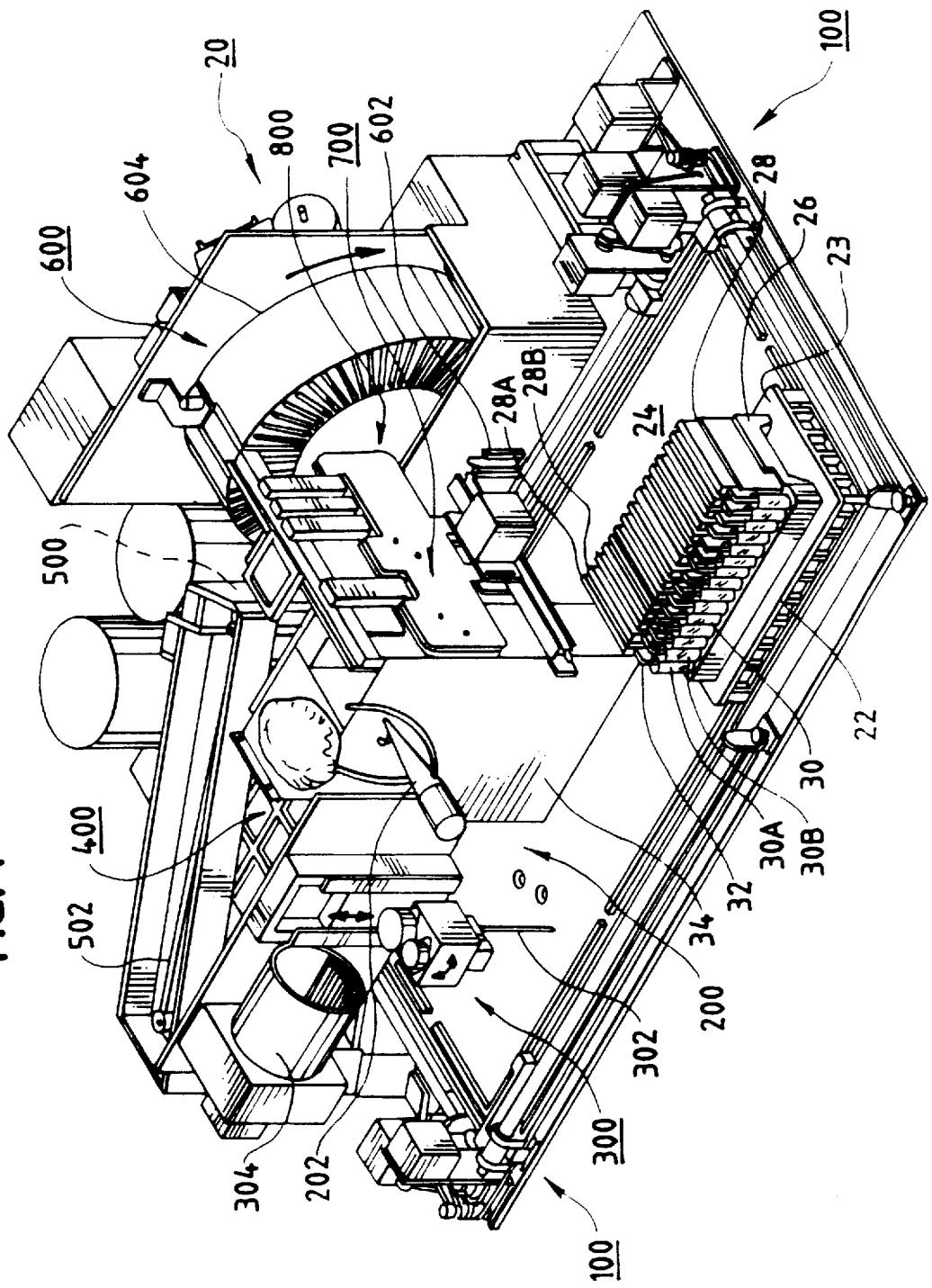
FIG. 1 is a perspective view of a preferred automatic biological sample testing machine that incorporates the optical reading and sample card transport systems of the invention.

FIG. 1 is a perspective view of a preferred biological sample testing machine 20. The following detailed description of the preferred embodiment of the inventive optical reader and sample card transport systems will be discussed in the context of the biological sample testing machine 20. It will be appreciated, however, that the principles of the invention may be used in other types of testing machines besides the preferred microbiological sample testing machine 20. Other possible implementations include chemical testing, immunochemistry, immunoassay, and nucleic probe assay machines.

The biological sample testing machine 20 includes a test sample positioning system 100, consisting of four independent motor-driven paddles, which is designed to slide a sample tray 22 (referred to herein as a "boat") across a base pan 24 around the machine 20 to several discrete stations, where various operations are performed on the samples in the boat 22. Prior to the start of the procedure, a technician loads a cassette 26 with a plurality of test cards 28 and receptacles such as test tubes 30 containing biological samples to be tested. Each test card 28 has an L-shaped transfer tube 32 protruding therefrom for permitting fluids containing the biological samples to be drawn from the test tubes 30 into the wells of the test cards 28. The technician places the loaded cassette 26 into the boat 22 at a loading station for the machine, such as the front, right hand corner of the base pan 24 shown in FIG. 1. The combined boat 22 and loaded cassette 26 are then moved as a unit over the surface of the base pan 24 about the machine 22 by the test sample positioning system 100.

In a typical microbiological testing scenario, described below for purposes of illustration but not limitation, the test cards 28 come in two varieties: (1) identification cards, in which particular different growth media are placed in the wells of the card 28 when the cards are manufactured, and (2) susceptibility cards, in which different concentrations of different antibiotics are placed in the wells of the card 28. The identification cards are used to identify the particular unknown biological agent present in the sample. The susceptibility cards are used to determine the susceptibility of the biological agent to various concentrations of antibiotics or other drugs. In the test procedure described below, identification and susceptibility tests can be performed on a single sample in one cycle of operation of the machine 20. To accomplish this, the cassette 26 is loaded such that a test tube 30A containing a biological or control sample, connected via a transfer tube 32 to an identification card 28A, is placed adjacent to a test tube 30B connected via a transfer tube 32 to a susceptibility card 28B.

The cards 28 preferably contain or may have affixed bar codes across the top of the card for reading by a bar code reader built into the machine 20. The bar codes are unique to each card, and identify card information, such as card type, expiration date, serial number, and are used to correlate test data from the cards with the patient and the biological sample. In addition, the entire boat or cassette may have sample information for all of the cards loaded in the cassette stored on a memory device affixed to the cassette 26, such as a memory button or "touch button" available from Dallas Semiconductor Corp., 4401 S. Beltwood Parkway, Dallas Tex.

In the representative example shown in FIG. 1, seven or eight of the test tubes 30 in the boat 22 contain biological samples, and are in fluid communication with identification cards 28 by the straw-like transfer tube 32. The biological sample test tube 30A and its associated identification card 28A can be thought of as a set. The biological sample test tubes and identification cards are typically arranged in an alternating pattern in the cassette 26. Each biological sample test tube 30A and identification card 28A set is adjacent to an empty test tube 30B placed in communication with a susceptibility card 28B via a transfer tube 32. It will be appreciated that the cards and associated test tubes could be ordered in any order in the cassette 26 depending on the particular testing requirements for the samples. For example, the cards could be arranged as follows: identification (ID), susceptibility (SU), ID, ID, ID, SU, SU, ID, SU . . . Further examples would be all identification cards and all susceptibility cards.

The test sample positioning system 100 operates to move the boat 22 and cassette 26 over the base pan 24 first to a diluting station 200. The diluting station contains a rotating shot tube 202, by which a predetermined volume of diluent (such as saline solution) is added to the empty susceptibility test tubes in the cassette 26, e.g. test tube 30B. As the leading edge of the boat 22 is moved to the left during this process, it passes under a pipetting station 300. The pipetting station 300 includes a mechanism that automatically removes a pipette 302 from a source of pipettes 304, lowers the pipette 302 into the biological sample test tube 30A, and removes with vacuum a predetermined volume of biological fluid from the biological sample test tube 30A using the pipette 302.

The test sample positioning system 100 then moves the boat. 22 to the left by an amount equal to the separation distance between adjacent test tubes 30A and 30B, e.g. 15 mm. The pipetting station 300 then lowers the pipette 302 containing the biological fluid from the biological sample test tube 30A into the adjacent susceptibility test tube 30B (having already received a quantity of diluent from the diluting station 200), expels the fluid into the test tube 30B, and drops the pipette 302 into the susceptibility test tube 30B. The process of movement of the boat 22 by the test sample positioning system 100, adding diluent to the susceptibility test tubes 30B at the diluting station 200, and transferring of biological samples from the biological sample test tubes 30A to the adjacent susceptibility test tubes 30B at the pipetting station 300, continues until all of the identification and susceptibility test tubes sets (if any) in the boat 22 have been so processed. By virtue of the close spacing of the pipetting station 300 and the diluting station 200, simultaneous diluting and pipetting operations can be performed on multiple test tubes in a single boat 22. After the last pipetting operation has been performed, the test sample positioning system 100 then moves the boat all the way to the left-hand edge of the base pan 24.

It will be understood by persons skilled in the art that the cassette 26 may be loaded entirely with biological samples in the test tubes 30 and identification cards 28, such as the case where a batch of biological samples are to be tested to identify the contents of the samples. In this example, the diluting and pipetting operations are not necessary. However, in other types of sample testing, other diluents or fluids may be added to or withdrawn from the test tubes. In the example of where no diluting or pipetting operations are performed, the cassette 26 is loaded with test tubes and cards, and the positioning system 100 would simply move the boat 22 and loaded cassette 26 directly past the diluting station 200 and the pipetting station 300 without stopping, all the way to the left hand edge of the base pan 24.

Once at the left hand edge of the base pan 24, the test sample positioning system 100 operates to move the boat 22 along the left hand edge to a vacuum station 400. The vacuum station 400 is seen better in FIG. 2, which is a perspective view of the machine 22 with the diluting station 200 and the pipetting station 300 removed. At the vacuum station 400, a vacuum chamber 402 is lowered onto the boat 22 such that the bottom surface of the vacuum chamber 402 sealingly engages the top peripheral surface 23 of the boat 22. Vacuum is applied to the chamber 402 under microprocessor control, causing air in the interior of the test sample cards 28 to evacuate out of their associated test tubes and to be withdrawn from the chamber 402. The vacuum cycle is precisely managed to optimize filling using a closed loop servo system to regulate the change of vacuum and timing of the complete cycle. After a predetermined period, the chamber 402 is vented to atmosphere under microprocessor control. The venting of the cards causes the fluid in the test tubes 30 to be drawn into the cards 28, filling the wells in the cards 28.

Figure 2:
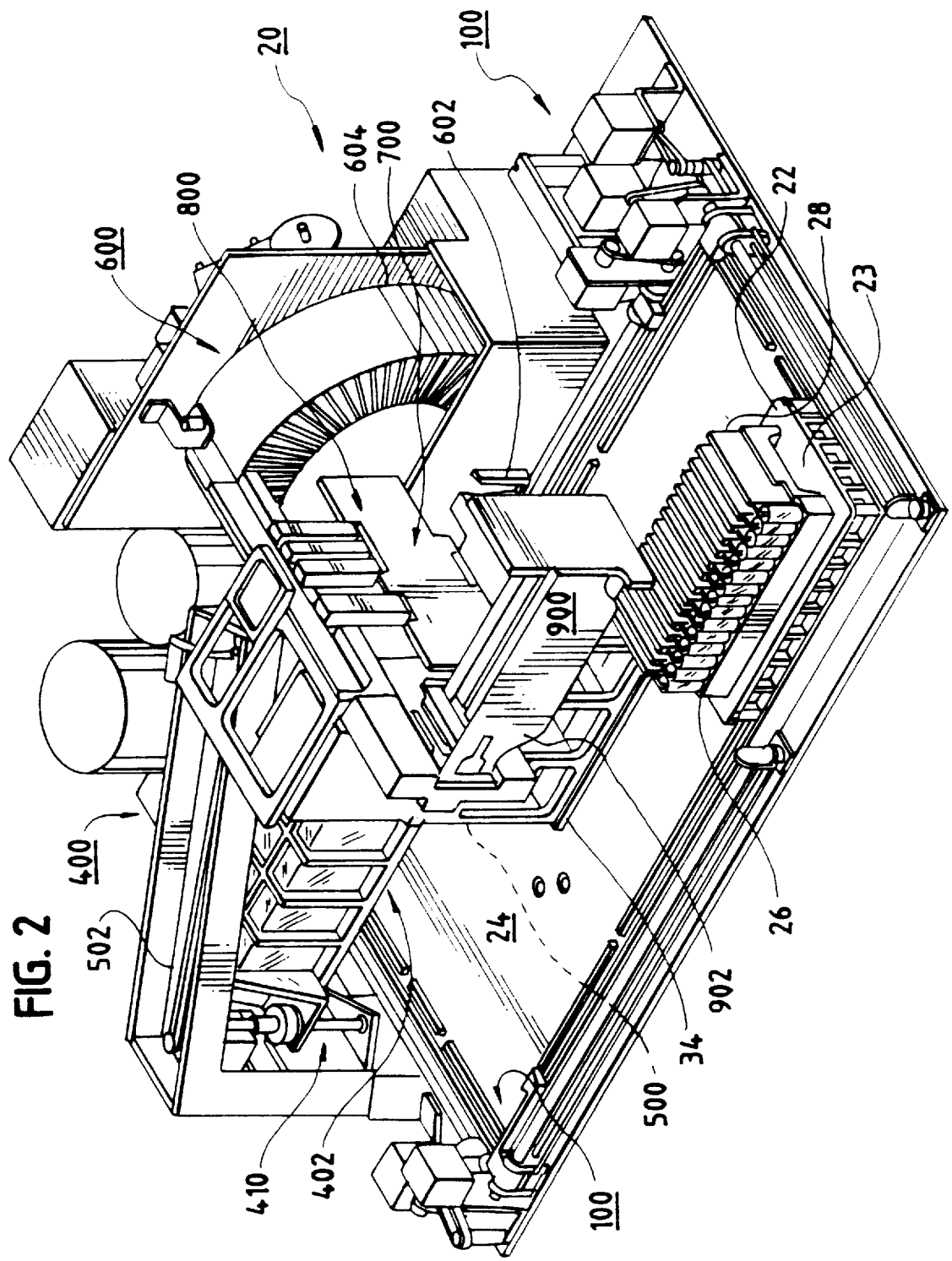
FIG. 2 is a perspective view of the machine of FIG. 1, with the diluting and pipetting stations removed to better illustrate the vacuum station of the machine.

The test sample positioning system 100 then operates to advance the boat 22 to the right across the rear of the base pan 24 to a cut and seal station 500, located behind the center mount 34 in FIGS. 1 and 2. The cut and seal station 500 consists of a hot cutting wire and attached support plate (not shown), and a drive mechanism 502 that lowers the cutting wire and support plate to the same elevation as the top portion of the transfer tubes 32 adjacent to where the transfer tubes 32 enter the test cards 28. As the boat 22 is advanced past the cut and seal station 500, the transfer tubes 32 are forced past the hot cutting wire. With the assistance of fore and aft constraints placed on the movement of the cards 28 by the walls of the cassette 26, and the lateral constraints on the movement of the card 28 by the cassette and wall structures of the machine 20, the hot cutting wire cuts the transfer tubes 32 by melting of the transfer tube material as the boat 22 is advanced past the hot cutting wire. A small stub of transfer tube material is left on the exterior of the card 28. The stub seals the interior of the card 28 from the atmosphere.

The test sample positioning system 100 then advances the boat 22 across the rear of the base pan 24 behind the center mount 34 to a carousel incubation station 600. A reciprocating cam driver is mounted to the center mount 34 opposite a slot 602 in the machine that pushes the cards off the cassette 26 one at a time through the slot 602 into a carousel 604. The carousel 604 is housed in an enclosure that is maintained at an incubation temperature of, for example, 35 degrees C. The enclosure is not shown in FIGS. 1 and 2 in order to show the carousel 604. The carousel 604 is rotated in synchronism with the movement of the boat 22 over the rear of the base pan 26 by the test sample positioning system 100, so as to place the next slot in the carousel 604 in line with the slot 602 opposite the next card in the cassette 26. If the carousel is only going to be partially loaded with cards, it may be advisable to load the cards into every other slot or two periodically in order to balance out the weight distribution in the carousel 604. For example, where the carousel has 60 slots and only 30 cards are to be processed, the cards are loaded into every other slot.

After all of the cards 28 have been loaded into the slots of the carousel 604, the boat 22 is advanced along the right hand edge of the base pan 24 back to its starting position (shown in FIGS. I and 2) for removal of the cassette 26 (containing the test tubes and transfer tubes remnants) and receipt of a new cassette.

As the cards 28 are being incubated in the incubation station 600, the cards are periodically, sequentially pushed out of the slots of the carousel 604 at the top of the carousel 604, one at a time, and moved by an optical scanner transport station 700 past a fluorescence and transmittance optics station 800. The wells of the card 28 are selectively subject to transmittance and fluorescence optical testing by the transmittance and fluorescence optics station 800. The transmittance and fluorescence optics station 800 includes detectors and processing circuitry to generate transmittance and fluorescence data for the wells in the cards 28, and to report the data to a central processing unit for the machine 22. If the test is not complete, the transport station 700 moves the card 28 back into its slot in the carousel 604 for more incubation and additional reading.

Generally, any given well in the card is subjected to either fluorescence testing or transmittance testing. A particular card 28 may have wells that require transmittance testing, and other wells that require fluorescence testing, hence the card is moved to both fluorescence substation and to transmittance substation. Other cards may require only transmittance testing, or fluorescence testing, and thus would be moved by the transport station 700 to the proper optical substation.

Typically, each card will be read every 15 minutes as the carousel makes one revolution. Typical incubation times for the cards 28 are on the order of two to eighteen hours, consisting of roughly four transmittance and fluorescence data sets per hour for each of the wells in the card 28 subject to the optical analysis.

After the testing is complete, the cards are moved by the optical scanner transport system 700 into a card output station 900 shown in FIG. 2. The card output station 900 consists of a detachable tray 902 that is placed to the side of the optical station 800 at approximately the same elevation as the optical station 800. The technician removes the tray 902 from the machine 20 as needed or when the tray 902 is full of cards, empties the cards into a suitable biohazard disposal unit, and replaces the tray 902 back into the machine 20.

Sample Card Transport Station 700

Figure 3:
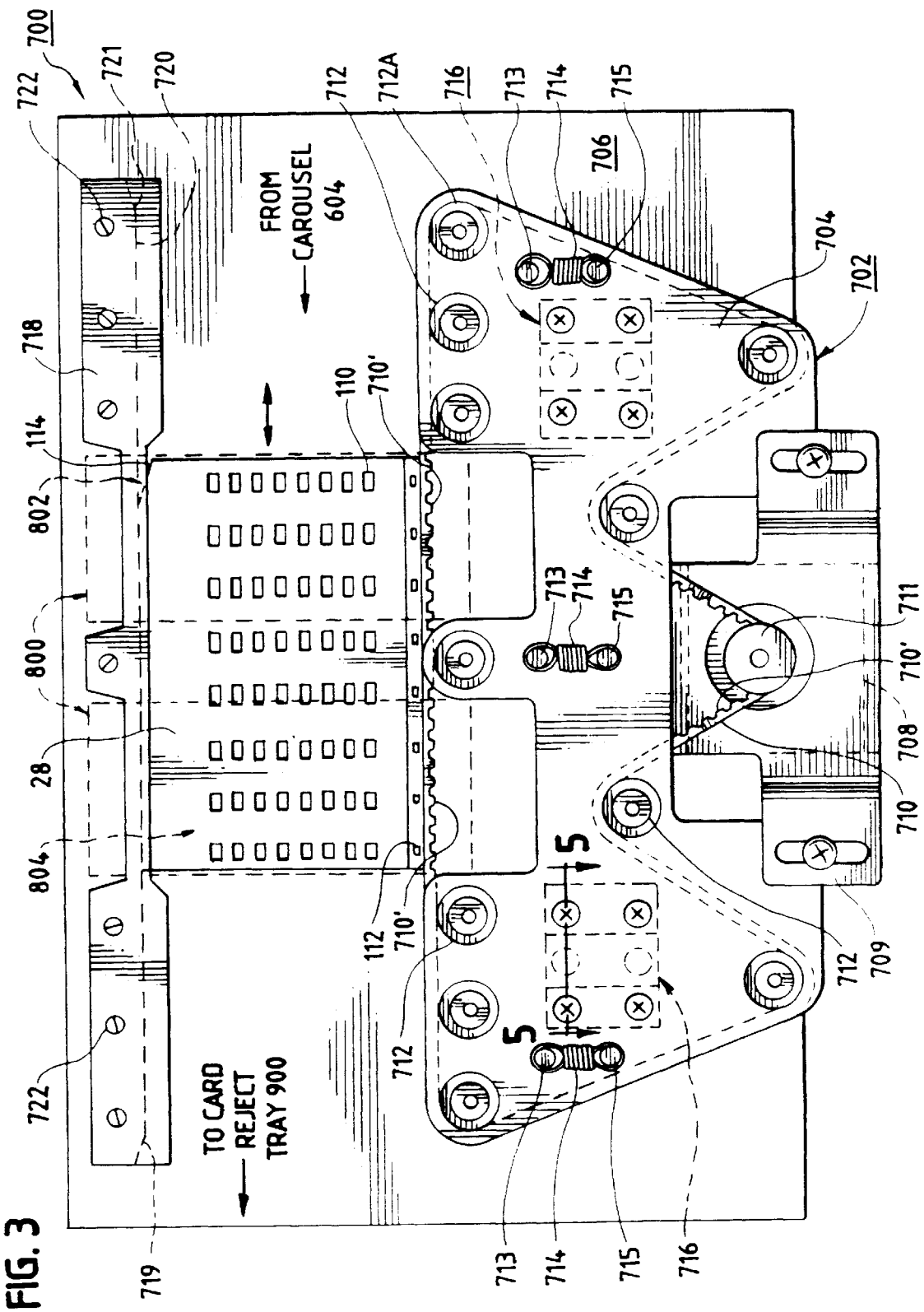
FIG. 3 is a plan view of a preferred sample card transport system for the machine of FIGS. 1 and 2.

Referring now to FIG. 3, the sample card transport station 700 is shown in a plan view. The station 700 includes a drive assembly 702 having a cover plate 704 which is mounted to a bulkhead or support 706. The optical reader system 800 in the preferred embodiment consists of a transmittance substation 802 and a fluorescence substation 804, which are mounted to the bulkhead 706. The sample card 28 is moved from the carousel 604 by the drive assembly 702 through the optical reader system 800 and back to the carousel 604 if the card 28 needs further incubation and additional reading. If the card has been sufficiently incubated based on the analysis of data from the optical reader system 800, the card 28 is moved to a card reject tray to the left of the optical system 800.

The drive assembly 702 consists of a stepper motor 708, shown in dashed lines, positioned behind a mounting bracket 709. The motor 708 drives a timing pulley 711 that moves an endless, substantially inelastic, drive belt 710 having teeth 710 over a series of rollers 712. The belt 710 is supported at the top of the cover plate 704 by a set of rollers 712. The path of the belt through the rollers 712 is shown in dashed lines in FIG. 3. It can be seen that the belt 710 passes across the top of the cover plate 704 and through the optical substations 802 and 804. The drive belt 710 engages the bottom edge of the card 28 along the top of the cover plate 704. A suitable drive belt 710 can be obtained from the Gates Rubber Co., of Denver, Colo.

A ledge 718 mounted to the bulkhead 706 is provided above the belt 710 and the optical reading system 800. The ledge has a slot 720 which receives the upper edge of the card 28. The ledge 718 and slot 720 defines a card travel direction. When the card 28 is pushed out of the carousel 604, the card 28 is snugly positioned in the space between the slot 720 and the belt 710. The entire drive assembly 702, including cover plate 704, stepper motor 708 and drive belt 710, is movable relative to the support bulkhead 706. To permit the relative movement, a set of carriage and slide assemblies 716 are provided, one of which is shown in more detail in FIGS. 4 and 5. As seen in FIG. 5, each of the carriage and slide assemblies 716 includes a slide 730 mounted to the bulkhead 706 by a bolt 734. The carriage 726 is mounted to the cover plate 704 by a set of four screws 724. The carriage 726 slides relative to the slide member 730 by means of ball bearings 728 which slide along a groove 732. In the preferred embodiment, two of the carriage and slide assemblies 716 are provided, one on each side of the cover plate 704.

The entire drive assembly 702 is biased upwards towards the ledge 718 by biasing springs 714. The springs have a top end 713 engaging a pin 714A mounted to the bulkhead 706, and a bottom end 715 engaging a pin 714B mounted to the cover plate 704. Three springs 714 in all are preferred, and are placed at the center and sides of the cover plate 704. The springs 714 each have a spring constant K of 16.5 lbs/in., for a total of 49.5 lbs/in for the three springs. Small slots are provided in the cover plate to allow for movement of the pins 714A, B. The purpose of the springs 714 is to constantly maintain the proper upward pressure on the card 28 by the belt 710, such as in the case of some tolerance variation in the height of the cards. The drive belt 710 must provide enough upward force so as to permit the belt to engage the bottom of the card 28 and move the card along the slot, but not too much to cause binding by the drive motor or too little force, which would cause the belt to slip relative to the bottom of the card. By maintaining the proper upward force on the card, such that belt travel is directly translated into card travel, precise movement by the stepper motor 708 results is precise movement of the card 28 relative to the optical system 800. This precise movement is discussed in greater detail in conjunction with the operation of the transmittance substation 802.

Figure 4:
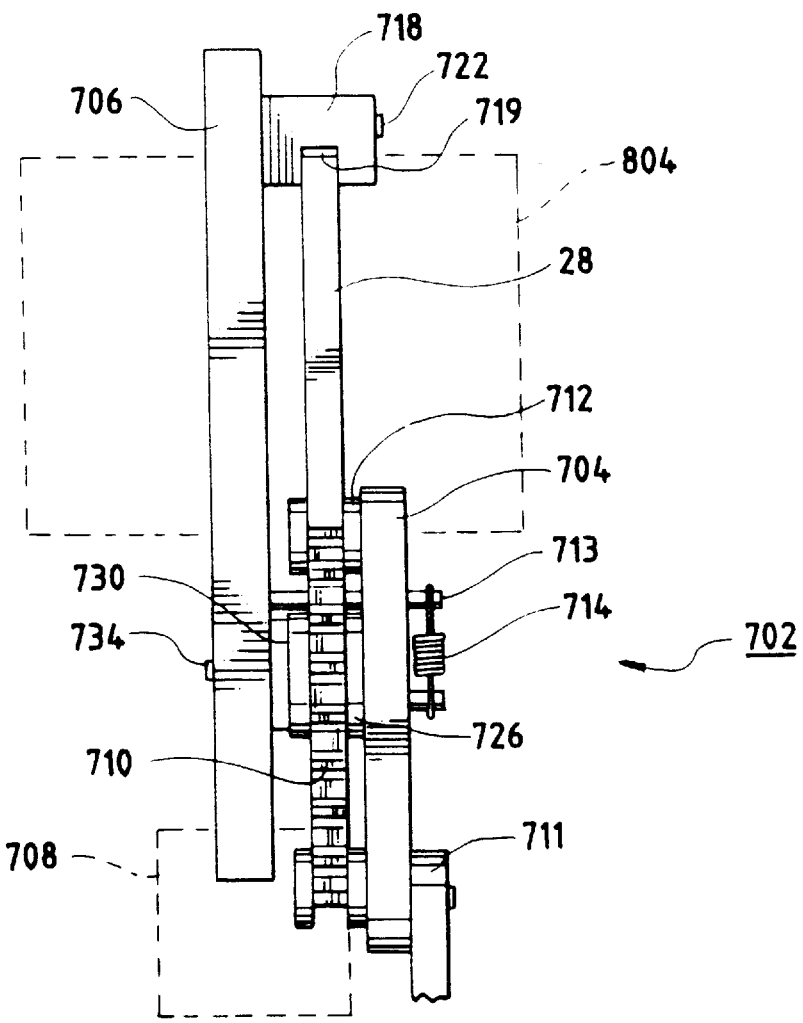
FIG. 4 is a side view of the sample card transport station of FIG. 3, looking in the direction of the carousel and incubation station of FIGS. 1 and 2.
Figure 5:
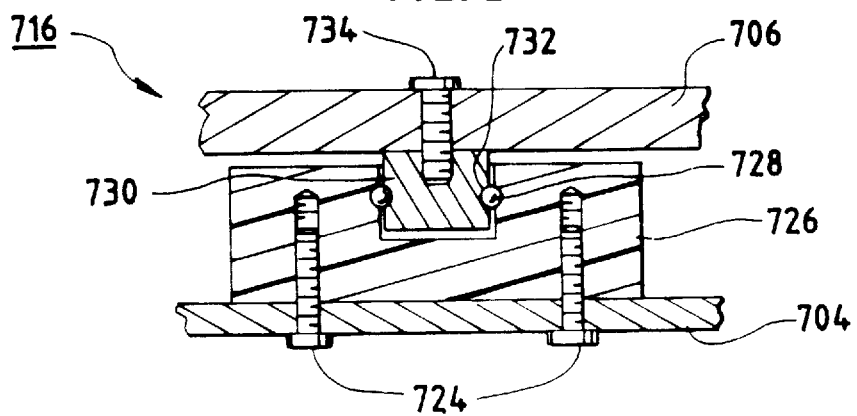
FIG. 5 is a sectional view of the carriage and slide assembly of FIGS. 3 and 4, which permits the drive subassembly to move relative to the bulkhead.

Referring to FIG. 4, the drive assembly 702 and bulkhead 706 are shown in a side view, looking towards the carousel 604 and incubation station 600 of FIGS. 2 and 3. The rollers 712 at the top of the cover plate 704 form a slot, as shown, which helps support the bottom edge of the card 28. The card 28 is snugly positioned between the belt 710 and the slot 720 in the ledge 718. The upward force on the card 28 by the springs 714 causes the belt 710 to grip the bottom edge of the card 28, such that the card 28 is slid along the ledge 718 by the drive belt 710 without any slippage between the belt 710 and the card 28. To facilitate the sliding motion, the slot 720 (FIG. 3) is made from a low friction material such as Delrin or given a low friction coating. The bottom edge of the card 28 is provided with a knurled texture surface (e.g., small parallel raised ridges oriented perpendicular to the direction of card travel) to better enable the belt 710 to grip the card 28 as the belt 710 moves backward and forwards over the rollers 712. The top edge of the card 28 is smooth.

Referring again to FIG. 3, in order to place the card into the sample card transport system 700, a push mechanism is provided to push the card 28 out of the carousel 604. The push mechanism is shown in FIGS. 6B and 6C. FIG. 6B is a perspective view of the carousel 604 showing the push mechanism 648 mounted to the front of the carousel bulkhead 652, and FIG. 6C shows the mechanism 648 as seen from the rear of the bulkhead 652. The push mechanism includes an alignment block 654 mounted to the bulkhead 652 and a driver 656 that reciprocates back and forth relative to the block 654. A motor 648 having a gear 662 is mounted behind the bulkhead 652. The teeth of the gear 662 cooperate with a set of teeth 658 on the driver 656, such that rotation of the gear 662 backwards and forwards causes the driver 658 to move in the direction shown by the arrow 664 (FIG. 6C) in the space between a lower slot 666 and an upper slot 668 in the block 654. The end of the driver 656 is positioned in alignment with the top slot 614 in the carousel 604. When the driver 656 is operated by the motor 648 such that the driver 656 is pushed into the slot 614, the card 28 within the slot 614 is pushed out of the slot into the space between the ledge 718 and the drive belt 710. (The construction and operation of the reciprocating cam mechanism that loads the cards 28 into the carousel from the cassette 26 is essentially the same as that for the push mechanism 648). An optical detector 650 is provided directly above the slot 614 so as to control the rotation of the carousel 604 such that slot 614 is properly positioned adjacent the driver 656 and ledge 718.

The push assembly 648 slides the card 28 out of the slot 614 at the top of the carousel 604 and places the card 28 at the extreme right hand edge of the drive assembly 702 adjacent to the extreme upper right drive roller 712A. The stepper motor 708 is operated in a forward direction (rotating the timing pulling 711 in a counter-clockwise direction), causing the drive belt 710 to move to the left and move the card 28 to the left towards the transmittance substation 802.

When the leading edge of the card 28 reaches the transmittance substation 802, an optical interrupt LED in the transmittance substation transmits radiation through an optical interrupt aperture 112 at the base of the card 28. An optical interrupt detector senses the radiation and sends a signal to the control system to cause the motor 708 to stop. When the motor 708 stops, the first column of wells 110 in the card 28 are positioned directly opposite a set of eight transmittance LEDs in the transmittance substation 804, which conduct transmittance testing of the column of wells in the card 28.

After an initial illumination of the LEDs, the motor 708 is operated to rapidly move the belt 710 in a series of small steps, such that the transmittance optics illuminates the individual wells at a series of positions across the width of the wells. This precise movement of the cards 28 achieves a large set of data for the wells 110. The transmittance testing at multiple positions across the wells 110 will likely include a detection of any air pockets or debris, if any, in the wells, enabling the data processing system to detect and possibly reject an abnormal transmittance measurement.

Where fluorescence testing is called for, after all of the wells of the card 28 have been subject to the transmittance testing by transmittance substation 802, the motor 708 and belt 710 slide the card 28 to the fluorescence substation 804, wherein fluorescence testing of the wells 110 takes place. Depending on the test status, the card 28 is then either returned to the carousel 604 by moving the motor 708 and belt 710 in the reverse direction, or else the motor 708 and belt 710 are operated to move the card all the way to the left hand edge of the drive assembly 702 to place the card 28 in a card disposal mechanism.

Figure 6A:
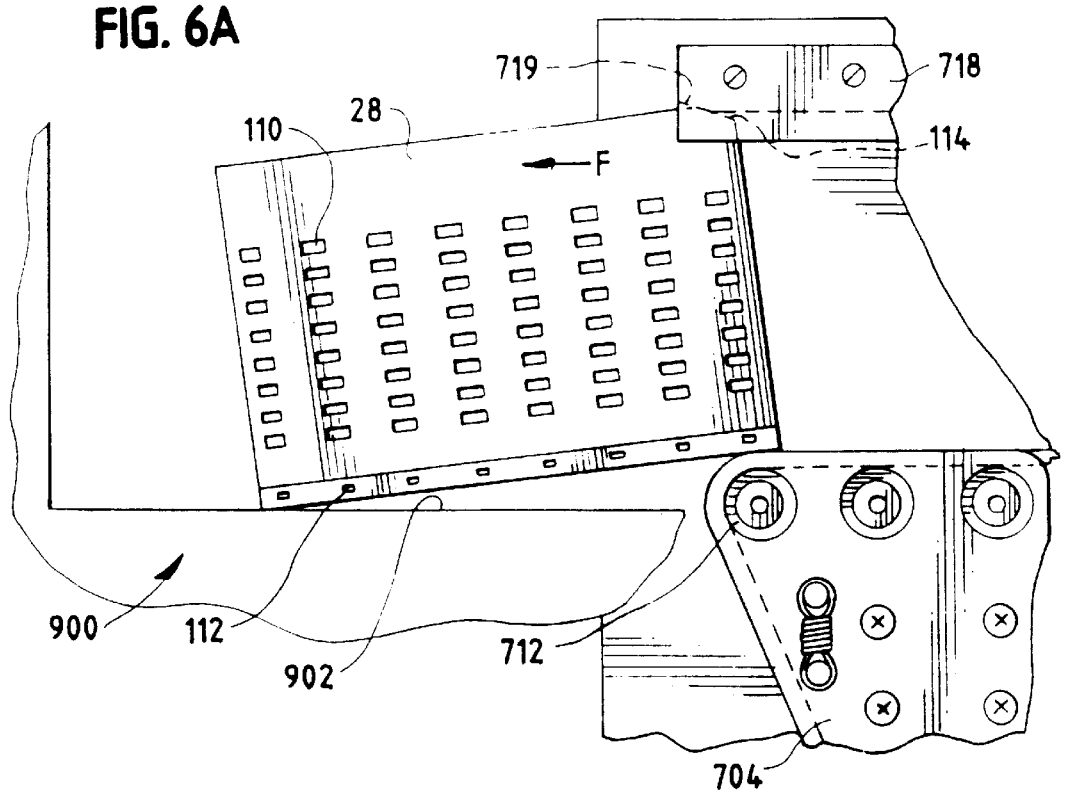
FIG. 6A is a plan view of the left-hand edge of the drive subassembly of FIG. 3 and 4, showing the ejecting of the card from the drive subassembly into a card reject tray.
Figure 6B:
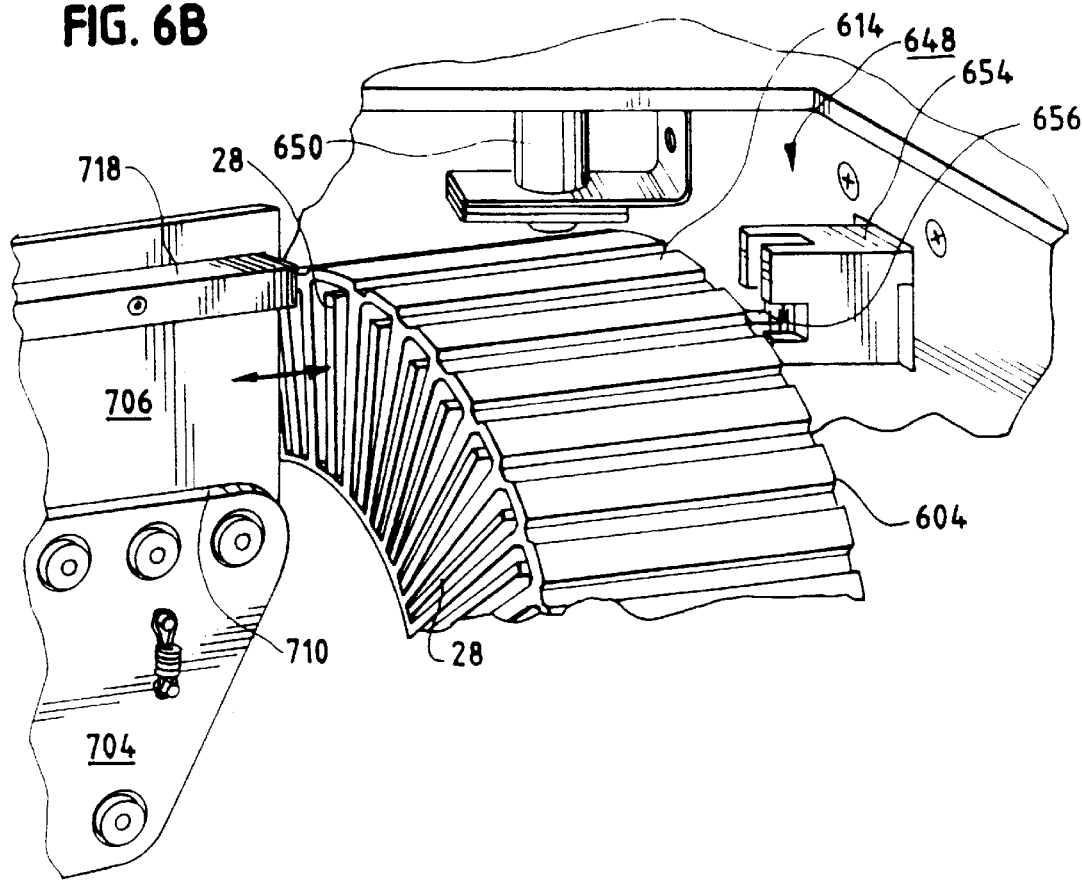
FIG. 6B is a perspective view of a push mechanism that pushes the cards out of the slots in the carousel of FIG. 2 into the sample card transport system of FIG. 3.
Figure 6C:
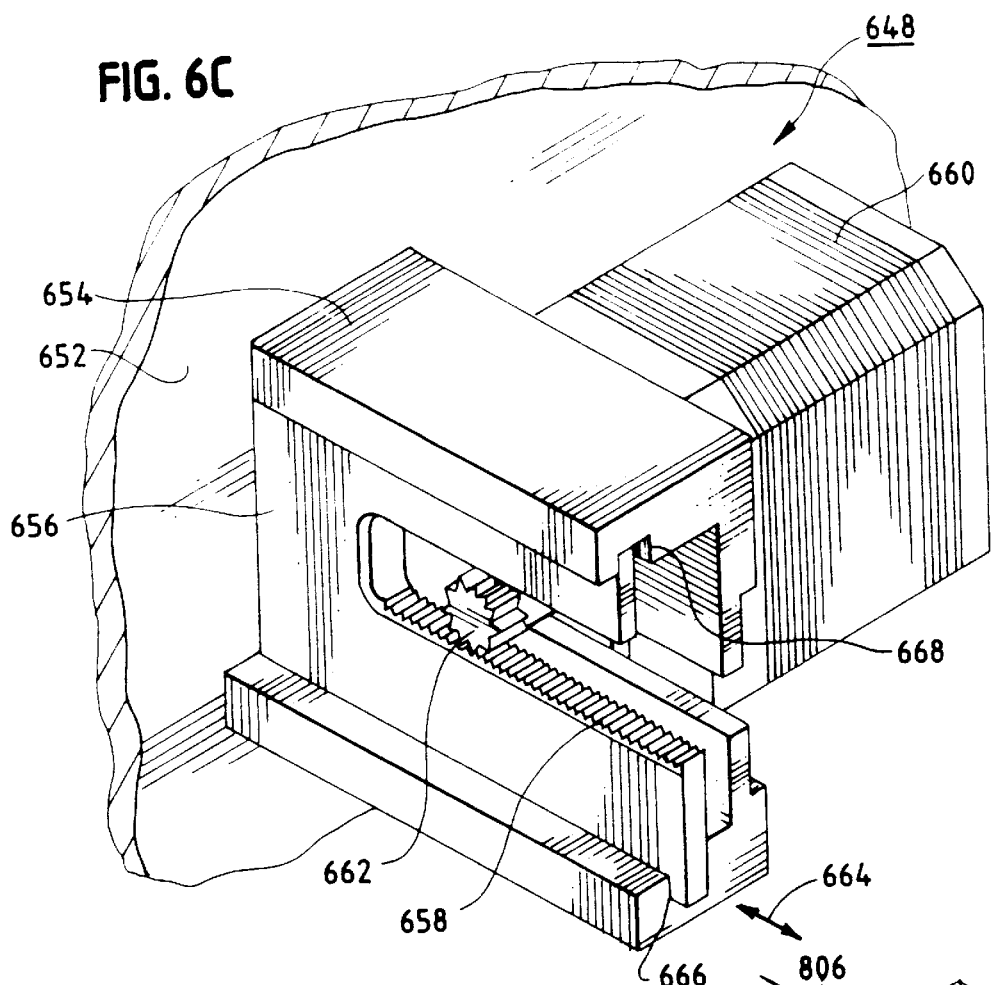
FIG. 6C is a perspective view of the push mechanism as seen from the rear of the bulkhead.

Referring now to FIGS. 3, 4, and 6A, the card disposal mechanism 900 has tray 902 in which the cards are stacked as they exit the sample card transport system 700. The ledge 718 is provided with a slant portion 719 at the extreme lefthand end of the ledge 718. When the card 28 is moved past the end of the cover plate 704 onto the tray 902, the upper right hand shoulder 114 of the card 28 is placed into contact with the slant portion 719. The tray 902 is slightly lower than the elevation of the belt 710 at the top of the cover plate 704, assisting the placement of the upper shoulder 114 against the slant 719. A resultant force F (FIG. 6A) is imparted to the card 28 by the drive belt 710 and slant portion 719, causing the card 28 to snap out of the drive assembly 702 into the card reject tray 902.

Fluorescence Optics Substation 804

Figure 7:
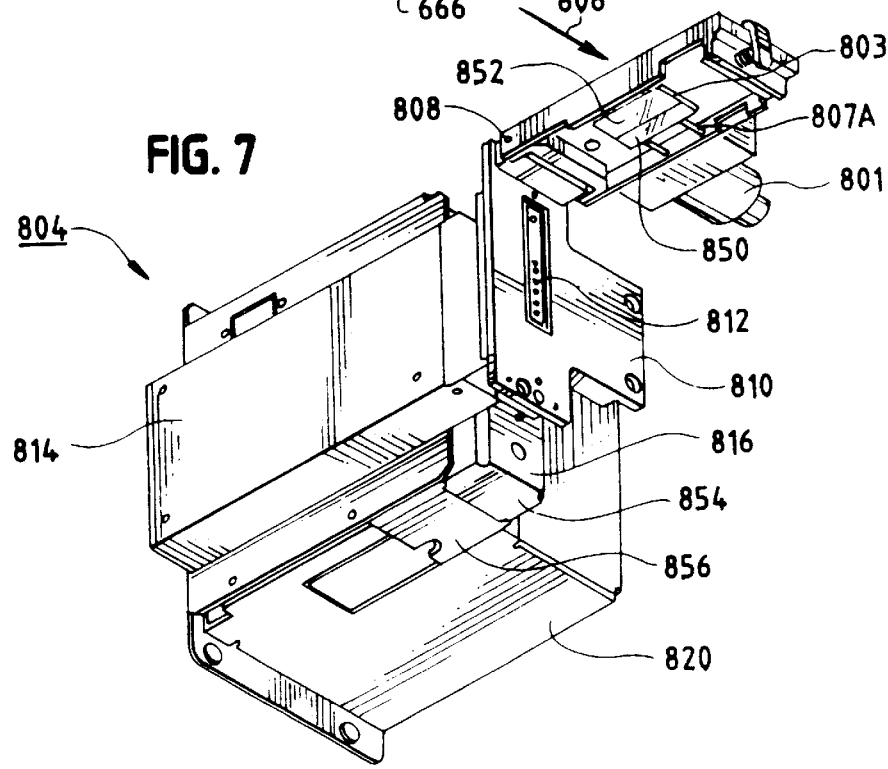
FIG. 7 is a perspective view of the fluorescence optical substation of the optical reading system of FIGS. 1 and 2, with the reflector assembly in an open position to better illustrate the optical head.

Referring now to FIG. 7, the fluorescence optics substation 804 is shown in a perspective view isolated from the machine 20. The substation 804 includes a selective reflector assembly 806 mounted via a hinge 808 to an optical head 810. The optical head 810 has a plurality of surface apertures 812 defining six optical channels between a fluorescence illumination source and the middle six wells in a column of wells 100 in the card 28. The placement and number of the optical channels depends on the lamp size (or number) and the geometry of the sample wells in the card 28. The illumination source is placed within a flashlamp cassette 816. An LED and detector cooperate with the optical interrupt aperture 112 along the base of the card 28 to precisely position the card in the space between the front surface apertures and the reflector assembly.

When the hinge 808 is in a closed condition, the selective reflector assembly 806 is positioned parallel to the apertures 812. The card 28 is moved back and forth in the space defined by the front surface apertures 812 and the reflector assembly 806.

The selective reflector assembly 806 has a stepper motor 801 which moves an optical shuttle 803 back and forth. A reflector 852 and a solid reference 850 are mounted to the optical shuttle 803. The purpose of the reflector and solid reference are described in more detail below.

Referring to FIG. 7A, the front of the selective reflector assembly 806 is shown isolated from the rest of the station 804 in a plan view. The optical shuttle 803 travels back and forth along a pair of guides 807A and 807B. In normal operation, the shuttle 803 is in a position such that the reflector 852 is placed directly opposite the apertures 812 of the optical head 810. Whenever a calibration of the detectors in the optical head 810 is performed, the motor 801 moves the shuttle 803 such that the solid reference 850 is placed in the optical path opposite the apertures 812. The selective reflector assembly housing includes a housing for an LED for the optical interrupt aperture 112 for the card 28. A spring clamp 805 is provided to secure the selective reflector assembly to the head 110 when the assembly 806 is in a closed condition.

FIG. 7B shows the rear of the selective reflector assembly 806. The selective reflector assembly 806 is shown in a side view in FIG. 7C. Behind the shuttle 803, a well 1000 is provided for a shaft (not shown) from the stepper motor 801. The stepper motor shaft passes through the gap 1002 in the well and is secured to a piece 809 extending upwardly from the rear surface of the optical shuttle 803. A cover plate (not shown) covers the well 1000 by mounting to the screw holes 1001. The back and forth motion of the shaft of the stepper motor 801 causes the shuttle 803 to slide back and forth along the guides 807A and 807B.

Referring again to FIG. 7, the removeable flash lamp cassette 816 holds an elongate xenon linear flash lamp, which serves as a fluorescence illumination source for the fluorophores placed in the wells 110 of the card 28. The flash lamp cassette 816 is connected to a high voltage power supply 820. The flashlamp 824 has a high current capacity connection allowing field replacement of the lamp. This is unique for this lamp type due to the high pulse currents generated during the flash (over 350 amps).

A peak detector 814 and electronics module is mounted behind the optical head 810. The flash lamp cassette 816 includes a interface block 854 and a lamp holder 856 which are shown in further detail in FIG. 9.

Referring now to FIG. 8, the fluorescence optics substation 804 is shown in a sectional view perpendicular to the axis of the flash lamp 824 and the six photodiode detectors. The flash lamp cassette 816 houses the xenon lamp 824, which is mounted at the focus of an elongate cylindrical parabolic reflecting mirror 822. The flash lamp radiation R is reflected off of a cold mirror 826 onto a 365 nM filter 828, which filters the radiation R to pass radiation at the excitation wavelength of the fluorophores. After passing through the filter 828, the radiation R reflects off a dichromatic beam splitter 830 along its optical path 833 and out of the apertures 812 and into the card wells 110. Any radiation passing through the wells 110 is reflected off the reflector 852 in the selective reflector assembly 806 and reflected back into the wells 110. The radiation excites the fluorophores in the well 110, causing the fluorophore to briefly to emit radiation. The emission radiation is shown as a dashed line in FIG. 8. The emission radiation passes through the dichromatic beam splitter 830, through a focusing lens 836 and band pass filter 838 onto a photodiode detector 840. There are six photodiode detectors in all for the six optical channels.

The use of a selective reflector 852 enhances the signal-to-noise ratio and minimizes optical cross-talk by doubling the optical path. Further, when the card 28 is positioned for reading by the fluorescence station by means of the optical interrupt, the wells in the card are oriented to promote optical separation of the wells to minimize optical cross-talk and maximize the fluorescence signal. The card 28 material is preferably opaque to minimize cross-talk, and white to maximize the fluorescence signal.

The dichromatic beam splitter 830 is highly reflective to radiation at the excitation wavelength of the fluorophores, reflecting approximately 95% of the radiation into the well 110. However, the dichromatic beam splitter 830 is highly transmissive to radiation at the emission wavelength of the fluorophores, passing most of the radiation from the fluorophore along the same optical path 833 onto the detectors 840.

Approximately 5% of the radiation from the lamp 824 that is not reflected off the dichromatic beam splitter 830 is transmitted along an optical path 834 to a mirror 832. The mirror 832 reflects the radiation through a focusing lens 836A and a band pass filter 846 to a reference photodiode detector 844. The reference detector 844 is used by the peak detector circuit 814 to compute the ratio of the signal detected by the detectors 840 divided by the signal detected by reference detector 844. The output of the lamp 824 may vary over time, however the ratio of the output of the channel detector 840 divided by the output of the reference detector 844 remains constant, i.e., independent of changes in lamp output over time. In addition to compensating for changes in lamp intensity, the reference channel 844 can also be used to determine if the lamp 824 is providing sufficient light for proper operation of the fluorescence optical system. By monitoring the lamp output at the reference detector 844, the system can automatically determine when the lamp 824 needs to be changed.

Figure 16:
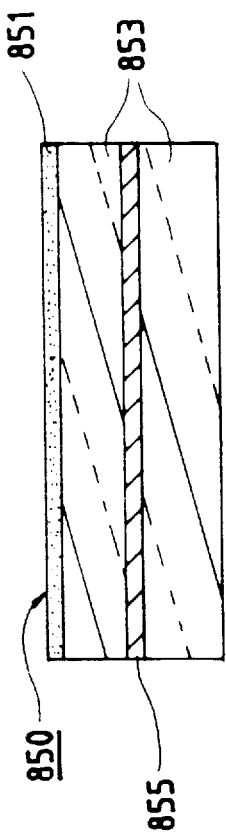
FIG. 16 is a cross section of the solid standard of FIG. 8.

Still referring to FIG. 8, the reflector assembly 806 also includes a solid reference 850 which emits radiation at the fluorophore emission wavelength when the reference 850 is moved into the optical path 833. The construction of a preferred sold reference is shown in FIG. 16. Preferably, the solid reference 850 is a phosphorescent Europium source sandwiched between glass plates 853 and having a 450 nM filter placed over the front surface of the glass.

Figure 17:
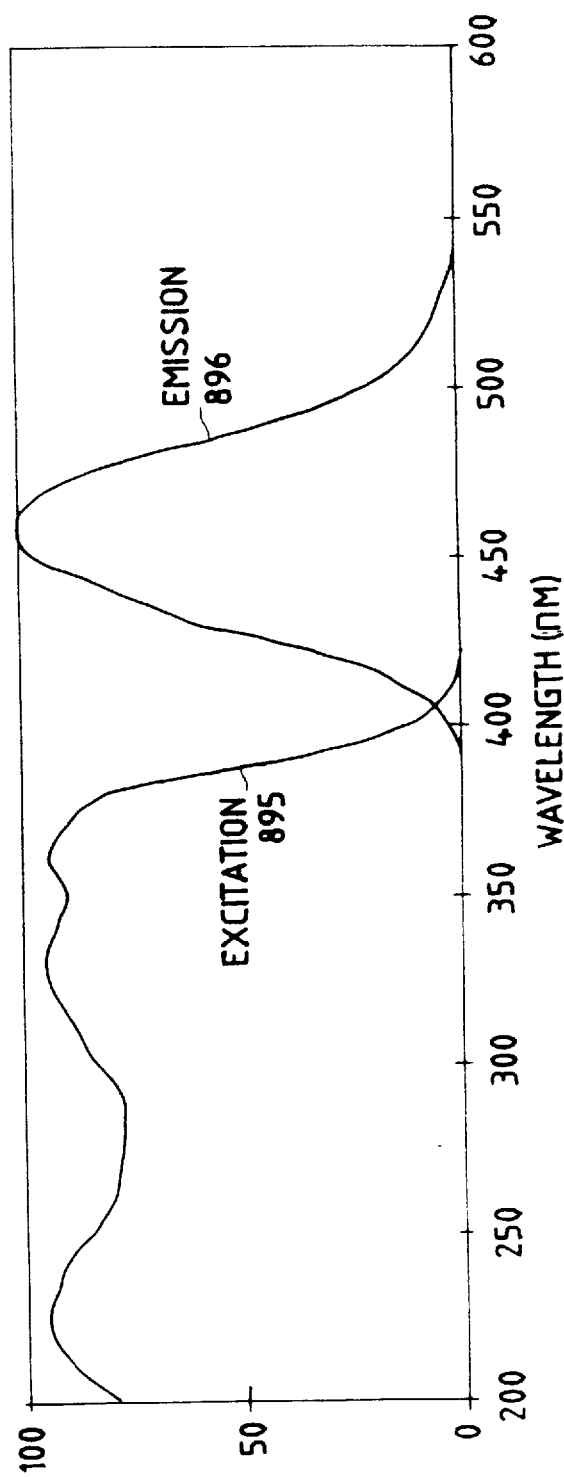
FIG. 17 is a graph of the excitation and emission spectra of the solid standard of FIG. 16.

Referring to FIG. 17, the typical excitation and emission of Europium is shown as a function of wavelength. Note from the excitation curve 895 that Europium responds to excitation radiation between 200 and about 375 nM. Thus, Europium excites at the wavelength that illuminates the fluorophores in the wells 110, i.e., about 365 nM. The Europium emission spectra 896 has a peak between about 455 and 460 nM, which substantially overlaps with the emission wavelength of the fluorophores in the wells 110 card 28. Thus, when the solid reference 850 is placed in the optical path 833 and the flash lamp 824 is flashed, the solid reference 850 emits radiation at an emission wavelength similar to that of the fluorophores in the wells 110 of the card 28. The solid reference 850 is thus used to compensate calibration of the output of the detectors 840, as described below.

It will be appreciated that other kinds of solid references could be used besides the Europium solid reference of FIG. 16. The choice of emission wavelength depends on the type of fluorophore that is used in the wells.

Figure 9:
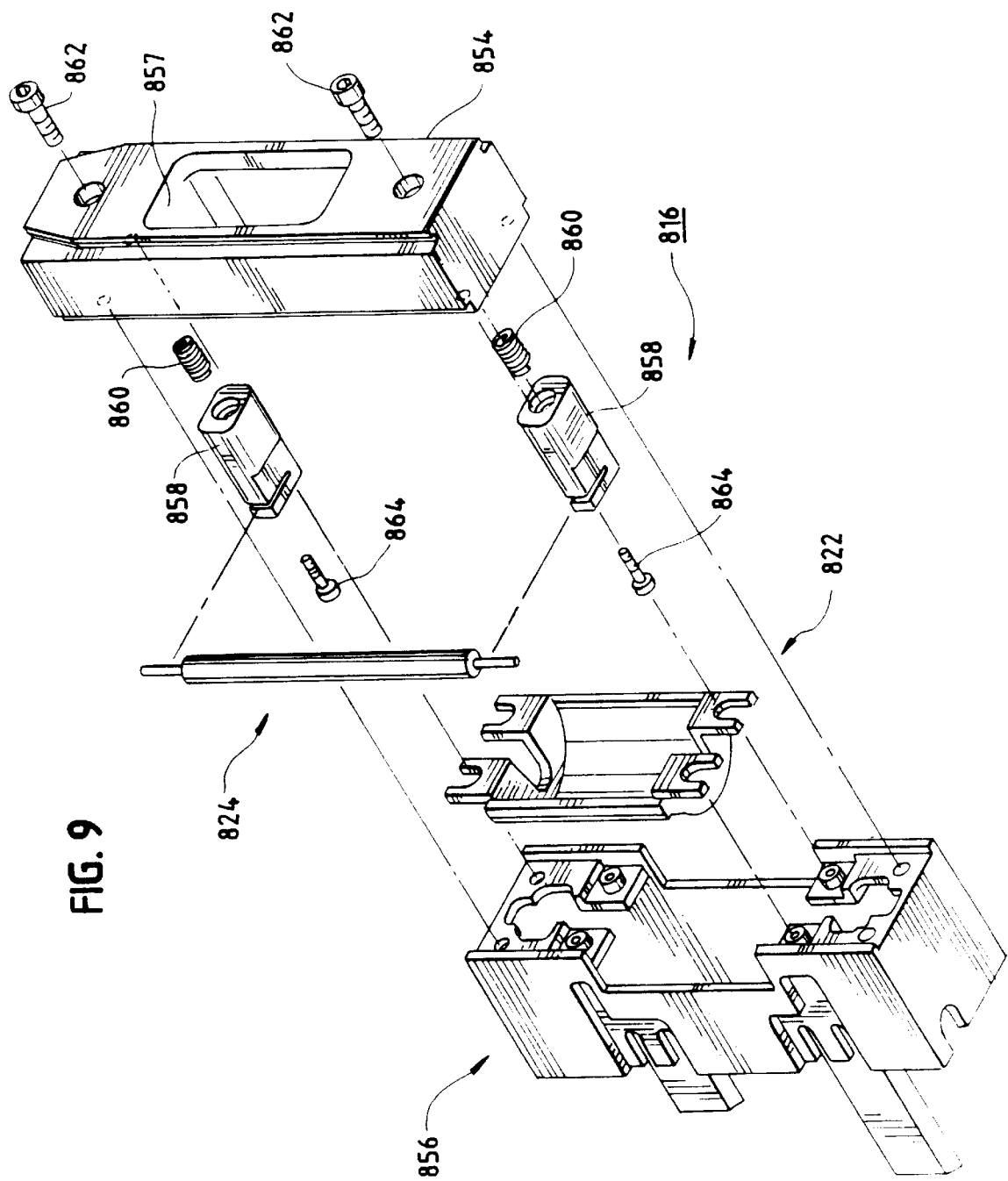
FIG. 9 is an exploded view of the flashlamp cassette of FIG. 7.
Figure 12A:
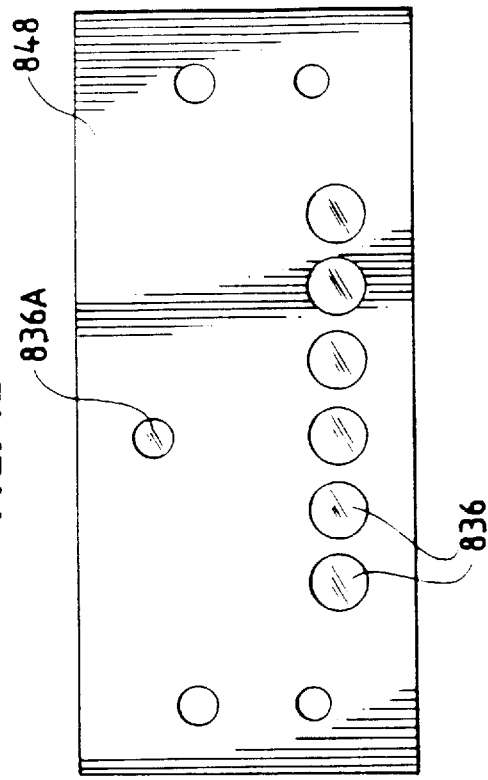
FIG. 12A is a top view of the lens assembly holder of FIG. 7.
Figure 12B:
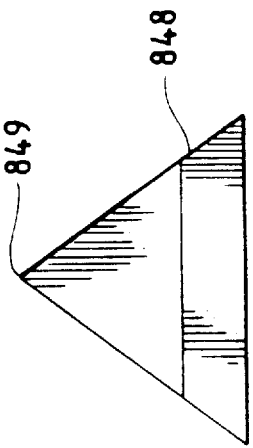
FIG. 12B is a rear view of the lens assembly holder.
Figure 12C:
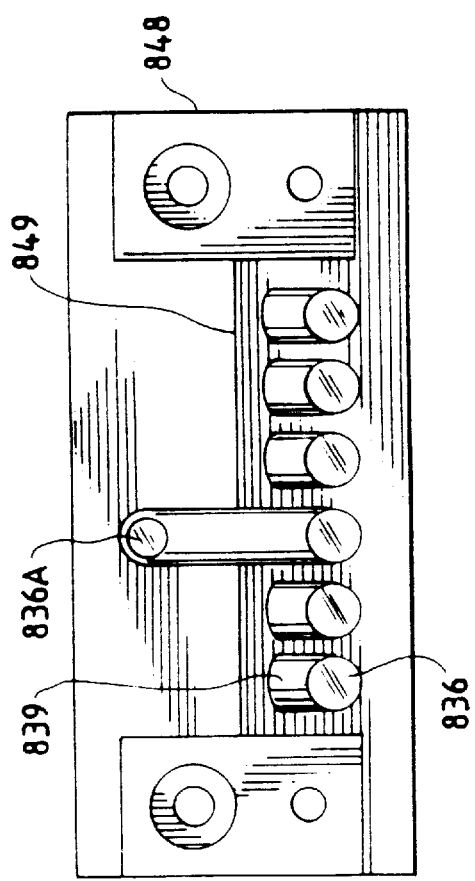
FIG. 12C is a side view of the lens assembly holder.
Figure 12D:
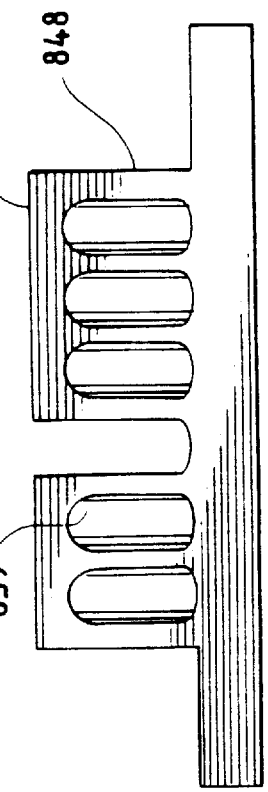
FIG. 12D is an end view of the lens assembly holder.

Referring now to FIG. 9, the flash lamp cassette 816 is shown in an exploded view. The flash lamp cassette 816 includes a lamp holder 856 which receives the parabolic reflector 822 for the flash lamp 8,24. The flash lamp 824 is mounted in a pair of adjustment pieces 858 and secured in place by mounting screws 864. The adjustment pieces 858 receive a pair adjustment springs 860 and adjustment screws 862. The adjustment screws 862 pass through apertures in the interface block 854 and seat in the adjustment pieces 858. By loosening and tightening the adjustment screws 862, the tilt of the flash lamp 824 relative to the cylindrical parabolic reflector 822 is adjusted so as to make the long axis of the lamp 824 lie at the focus of the cylindrical parabolic reflector 822. The interface block 854 includes an aperture 857 for allowing radiation from the flash lamp 824 to pass out of the interface block 854 and off the cold mirror 826 (FIG. 8) and towards the dichromatic beam splitter 830 and sample wells 110.

The optical head 810 is shown in FIGS. 10 and 11. FIG. 10 is a plan view of the face of the optical head 810 as seen from the card 28 as it passes the fluorescence substation 804. The head 810 includes a head plate 866 within which the apertures 812 and an optical interrupt aperture 811 are positioned. A photodetector is placed behind the optical interrupt aperture and is used in combination with the optical interrupt aperture 112 of the card 28 to determine when the card 28 is precisely positioned within the fluorescence substation 804. Referring now to FIG. 11, the rear of the head plate 866 is shown. The cold mirror 826 and dichromatic beam splitter 830 are placed within the optical head plate 866 and extend lengthwise across a set of six channels 837 positioned parallel in alignment with the middle six wells of a column of wells in the card 28.

Referring now to FIGS. 12A–12D, the lenses 836 and 836A of FIG. 8 are held by a lens holder piece 848. The lens holder 848 is shown in top plan view in FIG. 12A, a bottom plan view in FIG. 12B, a side view in FIG. 12C, and an end view in FIG. 12D. The lens holder 848 includes a peak portion 849 which fits behind the dichromatic beam splitter 830 (see FIGS. 8 and 11). The lenses 836 are placed at the base of curved walls 839, which cooperate with the channels 837 of FIG. 11 to form an optical pathway between the lenses 836 and the detectors 840 and 844. The walls 839 prevent crosstalk between adjacent channels by blocking light from adjacent channels.

Figure 19:
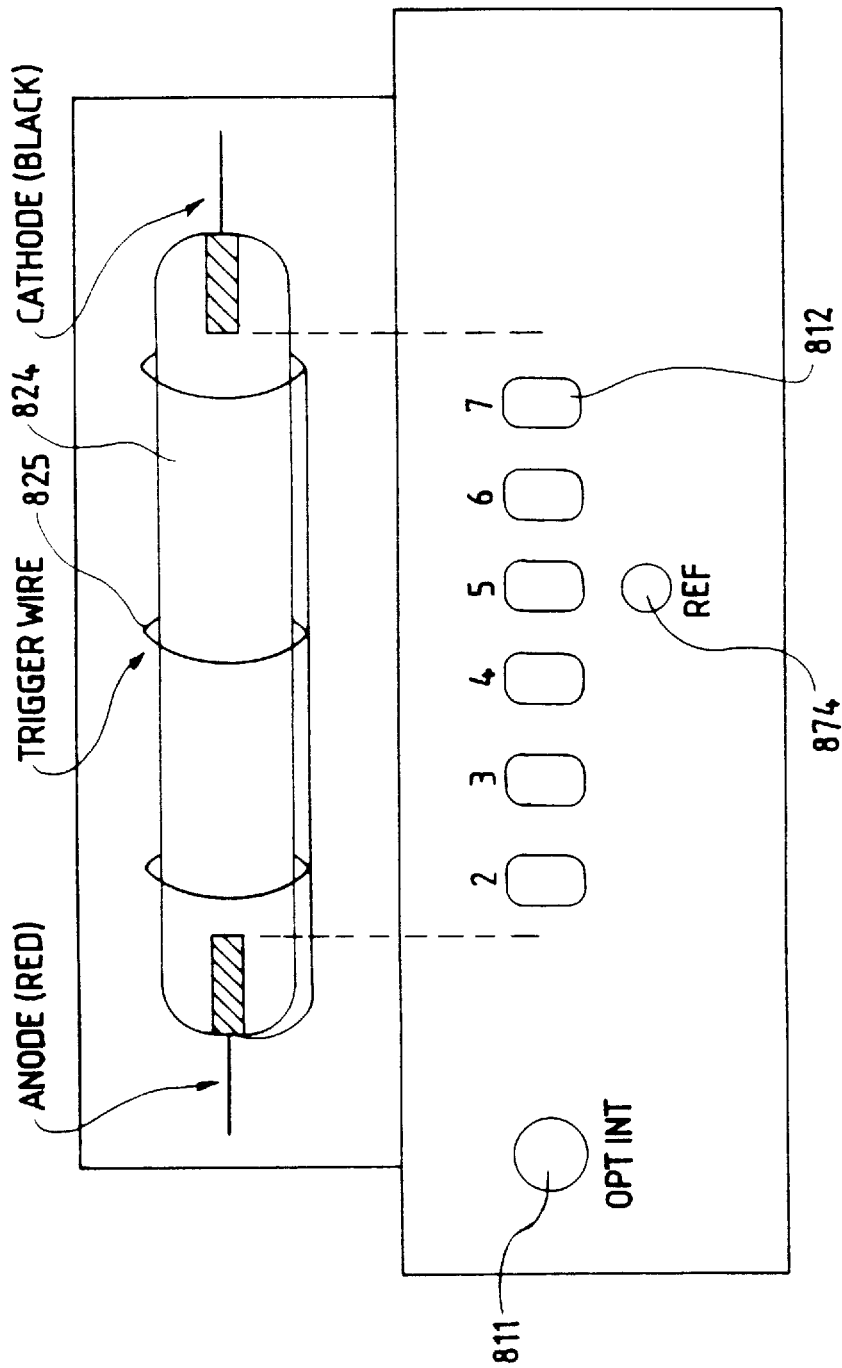
FIG. 19 is a schematic diagram showing the relationship of the flash lamp of FIG. 9 and the optical channels of the optical head of FIG. 8.

The relationship of the flash lamp 824 to the six optical channels is shown in FIG. 19. The flash lamp 824 is of sufficient length such that the space between the anode and cathode of the lamp 824 is greater than or equal to the distance between the six apertures 812 in the optical head. FIG. 19 also shows the relative placement of the optical interrupt 811 and the reference channel 874 relative to the six apertures 812. The flash lamp 824 has a trigger wire 825 wrapped around the surface of the lamp 824 that causes the lamp to flash. A suitable flash lamp 824 can be obtained from ILC Technology Inc. of Sunnyvale Calif., part no. L7752.

Referring now to FIGS. 13A and 13B, the fluorescence optical system 804 includes an optical interface block 868 which mounts behind the optical head 810 and the lens holder 848. The optical interface block 868 has an open region 870 to allow radiation from the lamp 824 (FIG. 8) to pass through the block 868 and off the cold mirror 826. The rear of the block 868 is shown in FIG. 13A, and includes six channels or passages 872 for the radiation from the six wells in the card, and a reference channel or passage 874 for the radiation 834 from the lamp 824 (see FIG. 8). The photodiode detector board 842 mounts on the rear of the block 868, as shown in dashed lines in FIG. 13A. Referring to FIG. 13B, the front of the block 868 includes a set of mounting pins 878 to mount the lens holder 848 to the block 868. The 445 nM bandpass filter 838 of FIG. 8 is secured in the block 868, as is the 365 nM bandpass filter 846 for the reference channel 874.

Referring now to FIG. 14A, the photodiode detector board 842 is shown in a plan view. The six photodiode detectors 840 are placed directly over the six channels 872 when the board 842 is mounted to the rear of the block 868 as shown in FIG. 8 and 13A. An optical interrupt detector 882 is provided to detect when light from an optical interrupt LED passes through the optical interrupt aperture 112 of the card 48, indicating proper alignment of the card 28 in the fluorescence substation 804.

Referring to FIG. 14B, the backside of the detector board 842 has conventional circuit traces 880 that receive the output of the photodiode detectors 840 and 844 and passes the signals to the peak detector 814 electronics.

Referring now to FIG. 15, the peak detector 814 of FIG. 7 is shown in a block diagram form. On the right-hand side of the illustration, the six optical channels CH1, CH2, CH3, CH4, CH5, CH6 represent the inputs from the six photodiode detectors. These signals are input into a set of six detectors and fixed gain amplifiers 844 that convert the current from the photodiode to a voltage signal. The reference channel input signal is supplied to a detector and amplifier 884A. The output of the detectors and fixed gain amplifiers are input into a set of variable gain amplifiers 886. Similarly, the output of the detector amplifier 884A is input to a variable gain amplifier 886A. The variable gain amplifiers 886 and 886A supply an output signal to a set of electronic peak detectors 888.

The peak detectors 888 are all basically the same as the peak detector described in the standard textbook, *The Art of Electronics*, by Horowitz and Hill, at page 218, FIG. 4.40, which is incorporated by reference herein. The standard circuit is modified slightly in that a transconductance amplifier is used as the first stage amplifier, instead of a standard operational amplifier. This device is a voltage-in, current-out amplifier that allows the circuit 888 to operate very fast with a minimum of signal distortion.

The output of the peak detectors 888 is buffered by a buffer amplifier and supplied to a multichannel input Analog to Digital (A-D) converter 890. The output of the peak detector 888A from the reference channel is similarly buffered and supplied to a reference input 892 in the A-D converter 890. A data bus 894 is provided which sends the output of the A-D converter 890 to a microprocessorbased controller board (not shown) which conducts the processing of the signals from the six channels and the reference photodetector. In particular, the controller board takes the ratio of the output of the six channels CH1 to CH6 divided by the output of the reference channel, to thereby compute a relative fluorescence measurements which is independent of the output of the lamp 824.

Once the card 28 is positioned in the fluorescence substation, the lamp 824 is flashed at a 25 Hz rate a number of times, such as ten times. After each flash, the A-D converter 890 computes the ratio of each channel to the reference and the controller board reads the results. After 10 flashes, the results are averaged for each channel. This process in conducted in parallel for each of the six channels.

The data bus 894 also supplies control signals to the peak detectors 888 and the variable gain amplifiers 886. In the calibration of the detectors, the controller board adjusts the variable gain amplifiers 886 so as to provide an output signal for each channel that matches the output signal when an initial calibration of the detectors was made. For example, at the time of the installation of the machine, the channels are calibrated with a card having wells filled with a control solution, and an initial reading of the detectors is stored in a memory.

Figure 18:
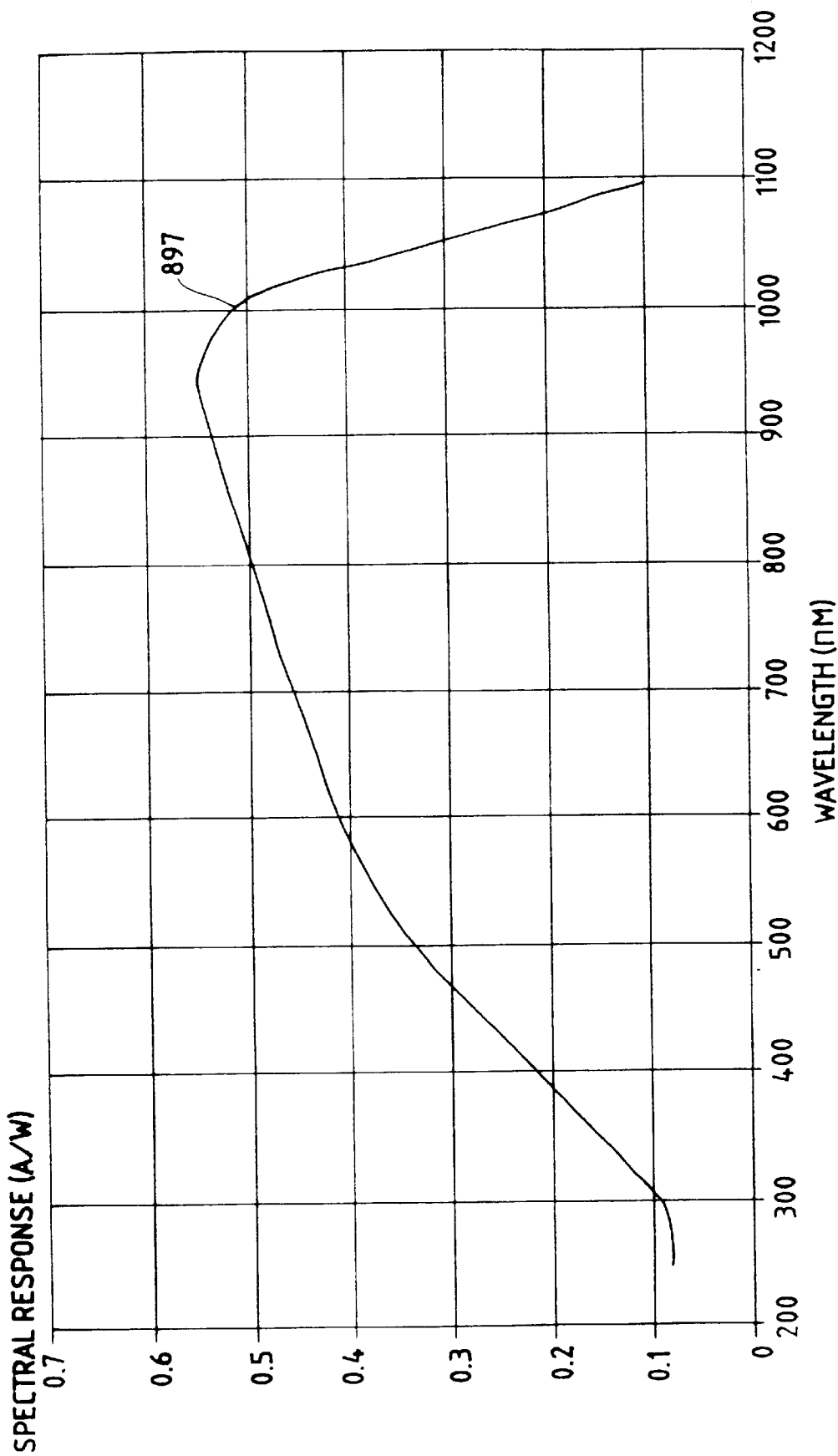
FIG. 18 is a graph of the responsivity as a function of incident radiation wavelength of the photodiode detectors of FIG. 14A.
Figure 20:
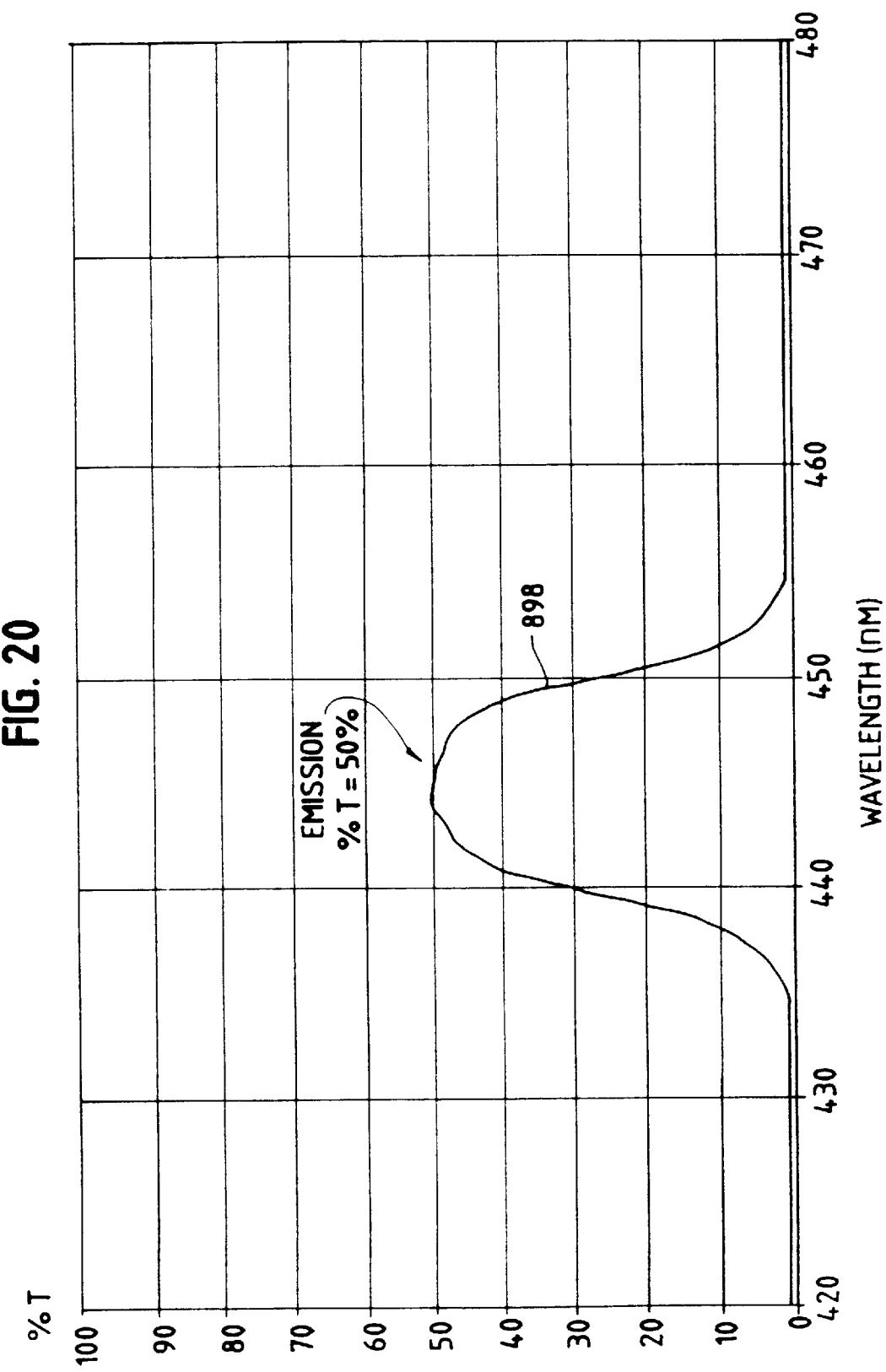
FIG. 20 is a graph of the filter transmittance as a function of wavelength for the 445 nM bandpass filter of FIG. 8.

The response curve for the detectors 840 is shown in FIG. 18. The response curve 897 has a typical spectral response (A/W) of between 0.2 and 0.35 in the 400 to 500 nM region of interest. The characteristics of the 445 nM pass filter 838 (FIG. 8) are shown in FIG. 20. The transmittance curve 828 has a maximum of 50% transmittance at 445 nM. The transmittance curve drops 828 off sharply below 440 nM and higher than 450 nM, preventing stray radiation from impinging on the photodiode detectors 840.

Figure 21:
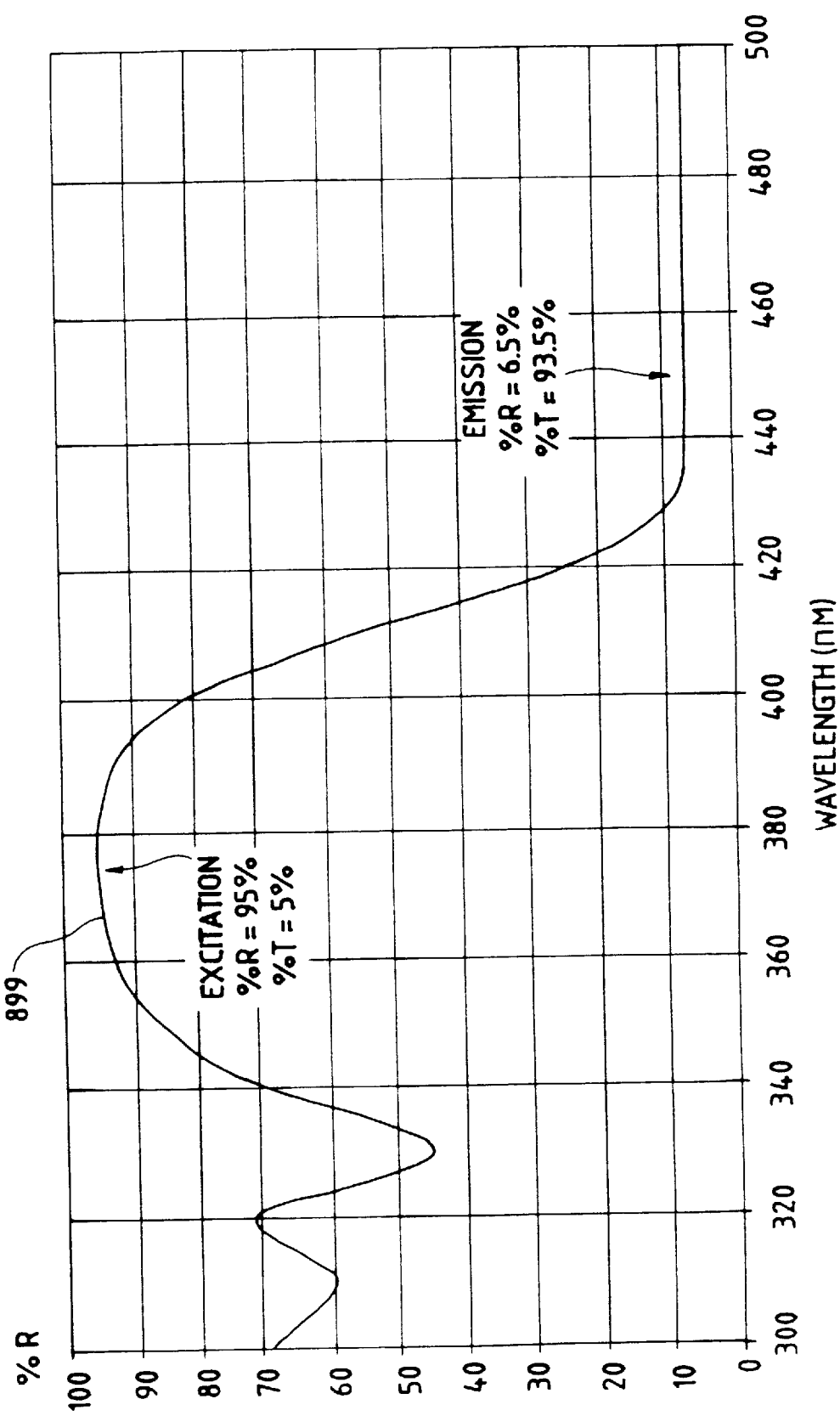
FIG. 21 is a graph of the reflectance (and transmittance) as a function of wavelength for the beam splitter of FIG. 8.
Figure 22:
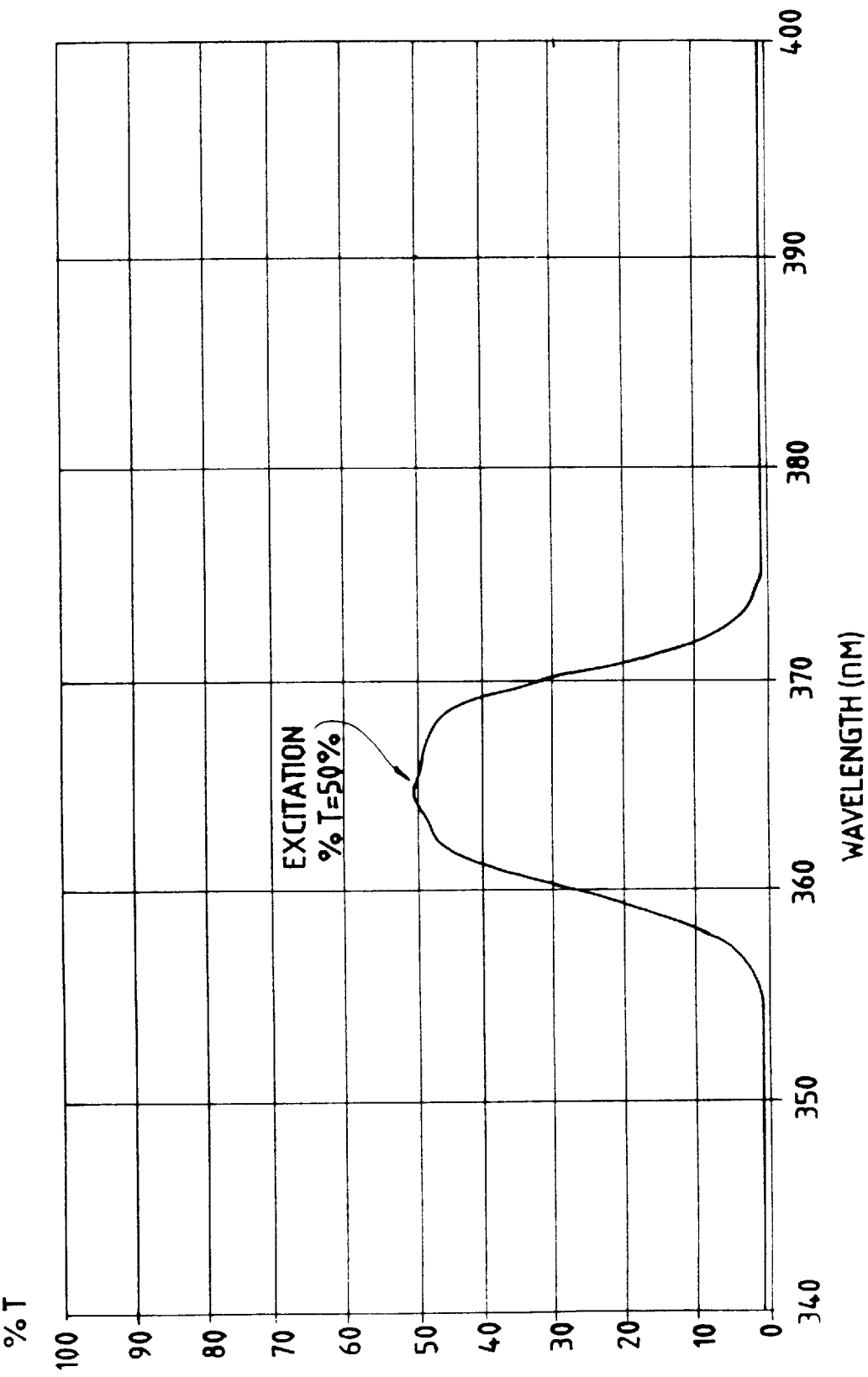
FIG. 22 is a graph of the filter transmittance as a function of wavelength for the 365 nM bandpass filter of FIG. 8.
Figure 23:
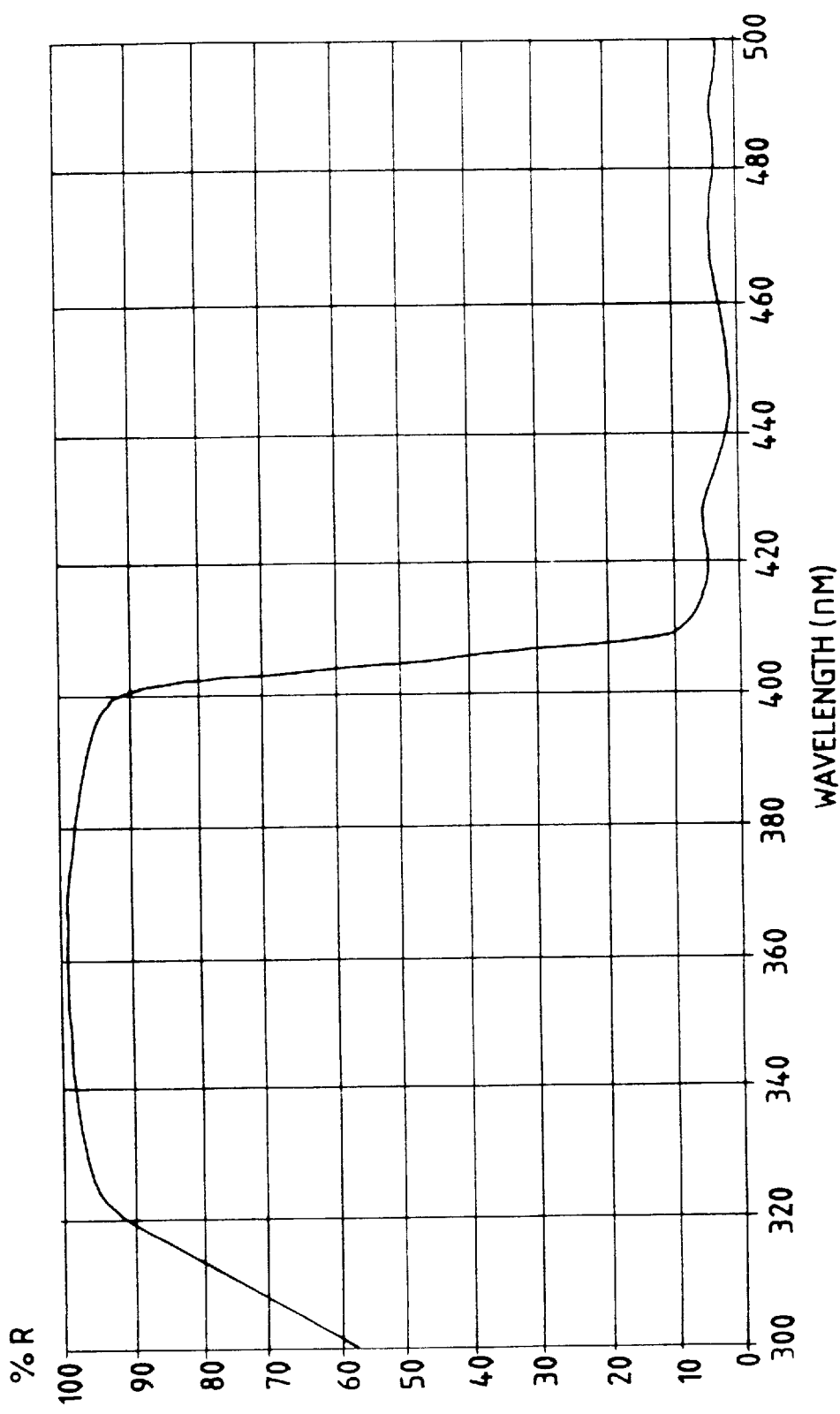
FIG. 23 is a graph of the reflectance as a function of wavelength for the UV cold mirror of FIG. 8.

The reflectance specifications of the dichromatic beam splitter 830 of FIG. 8 is shown in FIG. 21. The reflectance curve 899 shows a reflectance of 95% and a transmittance of 5% at the flashlamp output wavelength of 365 nM. The reflectance curve drops sharply above 380 nM to a low of about 6.5% reflectance and 93.5% transmittance at the emission frequency of the fluorophores, about 445–450 nM.

Thus, it can be seen from FIG. 21 that the dichromatic beam splitter 830 is highly reflective to excitation radiation from the flash lamp 824, but highly transmissive to emission radiation from the fluorophore in the card wells 110 and the solid reference 850.

Transmittance Substation 802

Figure 24:
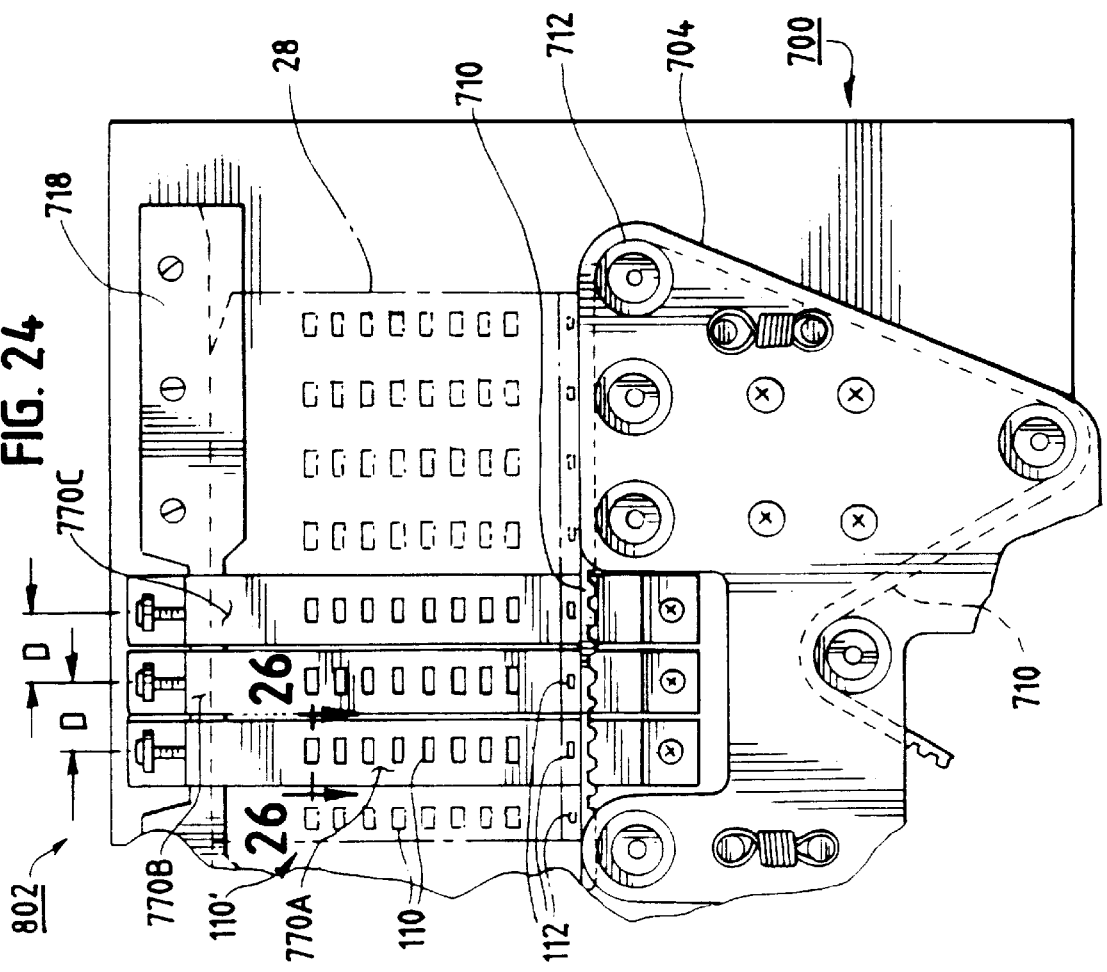
FIG. 24 is a detailed elevational view of the transmittance substation of FIG. 3.

Referring now to FIG. 24, a preferred transmittance substation 802 is shown in an elevational view. The substation 802 has three transmittance optical sources 770A, 770B and 770C, each of which comprise 8 LED sources and an optical interrupt LED source. The optical sources 770A–C are separated from each other by a separation distance D equal to the separation distance between the columns of wells 110 in the card 28. Three sources 770A–C are provided so as to enable transmittance testing at three different wavelengths. The source 770A is shown in perspective view in FIG. 25, and has eight LEDS 797 which are separated from each other by a distance L equal to the distance between adjacent wells 110 in the column direction of the card 28. The optical interrupt LED 789 shines light throughout the optical interrupt 112 along the base of the card 28. A set of three columns of transmittance detectors are placed behind the three sources 770A–C to collect radiation from the LEDs 797 and 789 and supply transmission data to the controller board in a well-known manner.

Referring now to FIG. 26, the transmittance source 770A and its associated detector 791 are shown in a sectional view in FIG. 26, taken along the lines 26—26 in FIG. 24. The LED source 797 is mounted to a substrate 798 in a well known manner and transmits light through the aperture 793 to the sample well 110. The radiation falls on the photodiode detector 791, which is also mounted to a substrate 792 in a well known manner. The detector 791 is mounted in a housing 795 that extends vertically directly opposite the detector 770A. The construction of light source 770A and detector 795 is the same for the other two sources and detectors in the transmittance station 802.

FIG. 27 is an enlarged, elevational view of the sample well 110, showing the pattern of transmittance radiation 790 that illuminates the well 110. Note that the illumination pattern 790 is only a fraction of the entire width of the well 110.

To perform transmittance analysis of the entire well 110, the card 28 is moved in a series of small increments relative to the source 770A, for example in 10 or 14 positions, and multiple illuminations of the well 110 are taken at each position. A presently preferred transmittance illumination test set is fourteen equidistant positions across the entire width of the well 110, and 10 illumination events at each of the fourteen positions. This test cab be performed at up to three different transmittance wavelengths for every well, resulting in a large set of transmittance data.

Figure 25:
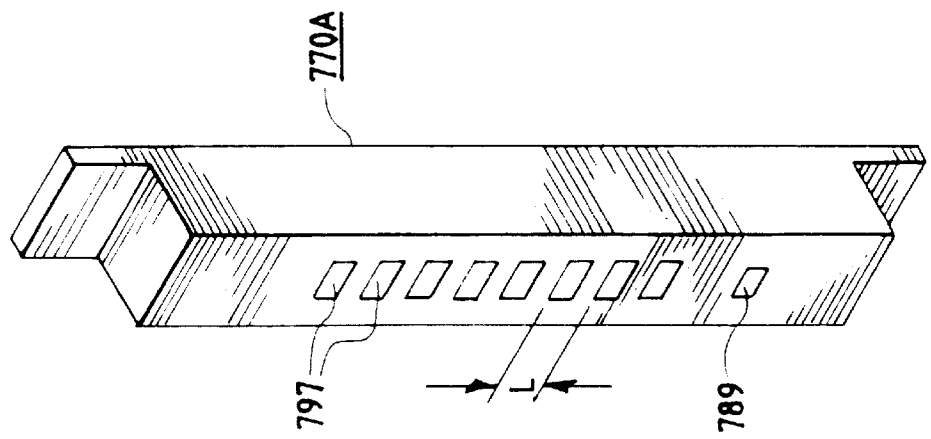
FIG. 25 is a perspective view of one of the three LED transmittance emission sources of FIG. 24.

Referring to FIG. 25, as the card 28 is moved out of the carousel 604, the first column 110' in the card is moved to the source 770C having LEDs of a first wavelength, whereby the 14 movement steps and 10 illumination events per step are performed. The card 28 is then advanced such that column 110' is positioned opposite the source 770B having LEDs of a second wavelength. The source 770B illuminates the first column 110' while the source 770C illuminates the second column. The card 28 is then moved such that the column 110' is positioned opposite the source 770A having LEDs of a third wavelength, and now sources 770A–C all operate in concert to illuminate three columns of the wells simultaneously. The card 28 is advanced to the left such that all columns are subject to transmittance illumination at the three sets of wavelengths. A column of LEDS could contain up to eight different wavelengths in one column if desired. When the last column has been illuminated by source 770A, the card 28 is moved to the fluorescence substation 804 for fluorescence testing, if necessary.

Of course, the operation of the transport system 700 and transmittance substation 802 could be controlled such that the card 28 is moved throughout the station 802 from left to right instead of right to left. Further, a lesser or even greater number of transmittance sources 770 could be used if desired.

A preferred test sample card is described in pending application Ser. No. 08/455,534, filed May 31, 1995,now U.S. Pat. No. 5,609,828, which is incorporated by reference herein.

Presently preferred and alternative embodiments of the invention have been described above. Persons of skill in the art will recognize that many variation from the preferred embodiments in terms of mechanical, electrical or optical details may be made without departure from the true spirit and scope of the invention. This true sprint and scope is defined by the appended claims, to be interpreted in light of the foregoing.

We claim:

1. In a sample testing machine having an incubation station for storing and incubating a sample card having at least one sample well, a sample card transport system for automatically moving said sample card from said incubation station to a fixed optical station for reading said sample card, comprising:

a means for ejecting said sample card from said incubation station;

a drive system receiving cards from said incubation station ejected by said ejecting means and comprising means for moving said card from said incubation station in a linear fashion to said optical station wherein said optical station is operative to read said sample well;

said drive system comprising (a) a motor (b), a drive belt operative in a forward direction to move said sample card from said incubation station to said optical station, and in a reverse direction to move said sample card from said optical station back to said incubation station, and (c) a guide member, said test sample card positioned between said belt and said guide member as said test sample card is moved between said optical station and said incubation station;

said drive belt moving said sample card without substantial slippage between said drive belt and said card, thereby enabling said card to be moved with substantial precision relative to said optical station for reading of said well.

2. The system of claim 1, further comprising a card reject station disposed adjacent to said optical system, wherein said motor and drive belt are operable in a forward direction to transport said card from said optical station to said card reject station upon the completion of the reading of said sample card.

3. The system of claim 1, wherein said optical system comprises a transmittance optical system and wherein said motor and drive belt are operative to move said card in a plurality of discrete steps in said forward or said reverse direction so as to enable a plurality of transmittance measurements at different locations of said wells in said card.

4. In a sample testing machine having an incubation station for storing and incubating a sample card having at least one sample well, a sample card transport system for automatically moving said sample card from said incubation station to a fixed optical station for reading said sample card, comprising:

a means for ejecting said sample card from said incubation station;

a drive system receiving cards from said incubation station ejected by said ejecting means and comprising means for moving said card from said incubation station in a linear fashion to said optical station wherein said optical station is operative to read said sample well;

said drive system comprising a motor and a drive belt operative in a forward direction to move said sample card from said incubation station to said optical station, and in a reverse direction to move said sample card from said optical station back to said incubation station;

said drive belt moving said sample card without substantial slippage between said drive belt and said card, thereby enabling said card to be moved with substantial precision relative to said optical station;

wherein said card defines first and second edges, and wherein said drive system further comprises:

a ledge extending transversely above said optical system and maintaining alignment of said card relative to said optical system, said ledge defining a card slot and a card travel direction, said card slot receiving said first edge of said card;

said drive belt movable relative to said ledge in a direction parallel to said card travel direction, said drive belt engaging said second edge of said card to move said card relative to said optical system; and a plurality of rollers supporting said drive belt.

5. The system of claim 4, further comprising:

spring means for biasing said rollers and said drive belt towards said ledge means so as to maintain pressure between said first and second card edges, said ledge and said belt;

said drive belt sliding said card relative to said ledge in said card travel direction without substantial slippage between said drive belt and said second edge of said card, thereby permitting said motor to move said card relative to said optical system with substantial precision.

6. In a sample testing machine having an incubation station for storing and incubating a sample card having at least one sample well, a sample card transport system for automatically moving said sample card from said incubation station to an optical station for reading said sample card, said optical station comprising a single light source and a detector for said sample well, comprising:

a drive system for moving said card from said incubation station in a linear fashion through said optical station wherein said single light source and detector are operative to read said sample well; and wherein said drive system is operative to move said card in a plurality of discrete steps while said well is in alignment with said single light source and said detector with said light source and detector operative in a plurality of illumination events at each of said steps so as to enable a plurality of optical measurements to be obtained at a plurality of different locations of said well in said card;

thereby permitting accurate readings of said well by said optical station.

7. The system of claim 6, wherein said optical station comprises a transmittance optical station.

8. The system of claim 6, wherein said well comprises an elongated oval shape and wherein drive system cooperates with said optical system to generate a plurality of measurements at 10 or more different positions of said well relative to said optical system.

9. In a sample testing machine having an incubation station for storing and incubating a sample card having at least one sample well, a sample card transport system for automatically moving said sample card from said incubation station to an optical station for reading said sample card, said optical station comprising a single light source and a detector for said sample well, comprising:

a drive system for moving said card from said incubation station in a linear fashion through said optical station wherein said single light source and detector are operative to read said sample well; and wherein said drive system is operative to move said card in a plurality of discrete steps while said well is in alignment with said single light source and said detector with said light source and detector operative in a plurality of illumination events at each of said steps so as to enable a plurality of optical measurements to be obtained at a plurality of different locations of said well in said card; and wherein said drive system comprises a motor driving a substantially inelastic and endless belt, and wherein said card is positioned snugly and directly between said belt and a ledge located opposite said endless belt, said belt and motor operative to slide said card relative to said belt without substantial slippage of said card relative to said belt, enabling said card to be moved relative to said optical system with substantial precision.

* * * * *